United States Patent
Han et al.

(10) Patent No.: US 11,391,268 B2
(45) Date of Patent: Jul. 19, 2022

(54) MUSCLE-POWERED PULSATION DEVICE FOR LONG-TERM CARDIAC SUPPORT

(71) Applicant: Carnegie Mellon University, Pittsburgh, PA (US)

(72) Inventors: Jooli Han, Pittsburgh, PA (US); Dennis Robert Trumble, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 415 days.

(21) Appl. No.: 16/617,706

(22) PCT Filed: Jun. 19, 2018

(86) PCT No.: PCT/US2018/038181
§ 371 (c)(1),
(2) Date: Nov. 27, 2019

(87) PCT Pub. No.: WO2018/236800
PCT Pub. Date: Dec. 27, 2018

(65) Prior Publication Data
US 2020/0121837 A1    Apr. 23, 2020

Related U.S. Application Data

(60) Provisional application No. 62/604,037, filed on Jun. 21, 2017, provisional application No. 62/603,984, filed on Jun. 19, 2017.

(51) Int. Cl.
*A61M 60/148*    (2021.01)
*A61M 60/40*    (2021.01)
(Continued)

(52) U.S. Cl.
CPC ........... *F04B 9/107* (2013.01); *A61M 60/148* (2021.01); *A61M 60/268* (2021.01);
(Continued)

(58) Field of Classification Search
CPC ........ F04B 9/107; F04B 43/067; F04B 45/02; F04B 9/127; F04B 9/14; F04B 43/12;
(Continued)

(56) References Cited

U.S. PATENT DOCUMENTS 5,443,504 A * 8/1995 Hill ..................... A61M 60/871
623/3.12
6,945,926 B2    9/2005 Trumble
(Continued)

OTHER PUBLICATIONS

Ambrosy et al., "The Global Health and Economic Burden of Hospitalizations for Heart Failure: lessons learned from hospitalized heart failure registries", J. Am. Coll. Cardiol., 2014, pp. 1123-1133, vol. 63:12.
(Continued)

*Primary Examiner* — Paula J Stice
(74) *Attorney, Agent, or Firm* — The Webb Law Firm

(57) ABSTRACT

A muscle-powered pulsation device for cardiac support including a muscle energy converter device including a piston arrangement for directing fluid out of an outlet of the muscle energy converter device using energy provided by a patient's muscle, and a hydraulic volume amplification device fluidly connected to the muscle energy converter device. The volume amplification device includes a casing including an inlet and an outlet, the inlet in fluid communication with the outlet of the muscle energy converter device, at least one resilient member positioned within an interior cavity defined by the casing, and at least one piston member movably and sealingly positioned within the interior cavity of the casing and operatively connected to the at least one resilient member, the at least one piston member separating the interior cavity into a first chamber and a second chamber.

26 Claims, 14 Drawing Sheets

(51) Int. Cl.
| | |
|---|---|
| A61M 60/268 | (2021.01) |
| F04B 9/107 | (2006.01) |
| F04B 43/067 | (2006.01) |
| F04B 45/02 | (2006.01) |

(52) U.S. Cl.
CPC ........... *A61M 60/40* (2021.01); *F04B 43/067* (2013.01); *F04B 45/02* (2013.01)

(58) Field of Classification Search
CPC ... A61M 60/148; A61M 60/268; A61M 60/40
See application file for complete search history.

(56) References Cited

U.S. PATENT DOCUMENTS

| | | | |
|---|---|---|---|
| 2002/0103413 A1* | 8/2002 | Bugge | A61M 27/002 600/16 |
| 2009/0216292 A1* | 8/2009 | Pless | A61N 1/3785 607/34 |

OTHER PUBLICATIONS

Aranda-Michel et al., "Design of a Muscle-powered Extra-aortic Counterpulsation Device for Long-term Circulatory Support", Proceedings of the 2017 Design of Medical Devices Conference, 2017, pp. 1-2.
Aranda-Michel et al., "Muscle-powered Extra-aortic Counterpulsation Device for Long-term Circulatory Support", Poster Presentation at the Design of Medical Devices (DMD) Conference, Apr. 12, 2017.
Boyle, "Current Status of Cardiac Transplantation and Mechanical Circulatory Support", Curr Heart Fail Rep., 2009, pp. 28-33, vol. 6.
Brown, "Medical Applications of Titanium and Its Alloys: The Material and Biological Issues", 1996, ASTM International, West Conshohocken, PA.
Han, et al., "Cardiac Assist Devices: Early Concepts, Current Technologies, and Future Innovations," Bioengineering, 2019, pp. 1-26, vol. 6:18.
Han et al., "Design of a Muscle-powered Soft Robotic Bi-VAD for Long-term Circulatory Support", Proceedings of the 2018 Design of Medical Devices Conference, Apr. 9-12, 2018, pp. 1-3.
Han et al., "Muscle-powered Counterpulsation Ventricular Assist Device (mVAD) for Long-term Cardiac Support", ASAIO Conference, 2017, pp. 1-2.
Han et al., "Muscle-powered Counterpulsation Ventricular Assist Device (mVAD) for Long-term Cardiac Support", Poster Presentation at ASAIO Conference, Jun. 23, 2017.
Han et al., "Ventricle-specific epicardial pressures as a means to optimize direct cardiac compression for circulatory support: A pilot study," PLoS One, 2019, pp. 1-12, vol. 14:7.
Hosseini, "Fatigue of Ti-6AI-4V", Biomedical Engineering-Technical Applications in Medicine, 2012, pp. 75-92.
Izzo et al., "In Vitro Testing and Evaluation of Intraaortic and Extraaortic Balloon Counterpulsation Devices", Proceedings of 1994 20th Annual Northeast Bioengineering Conference, 1994.
Kamada, et al., "Antihypertensive efficacy and safety of the angiotensin receptor blocker azilsartan in elderly patients with hypertension", Drug Chem. Toxicol., 2017, pp. 110-114, vol. 40.
Kung, et al., "Heart Booster: A Pericardial Support Device", Ann. Thorac. Surg., 1999, pp. 764-767, vol. 68.
Lahpor, "State of the art: implantable ventricular assist devices", Curr. Opin. Organ Transplant., 2009, pp. 554-559, vol. 14.
Legget et al., "Extra-Aortic Balloon Counterpulsation: An Intraoperative Feasibility Study", Circulation, 2005, pp. I-26-I-31, vol. 112.
Lloyd-Jones, "The Risk of Congestive Heart Failure: Sobering Lessons from the Framingham Heart Study", Curr. Cardiol. Rep., 2001, pp. 184-190, vol. 3.
Lloyd-Jones et al., "Lifetime Risk for Developing Congestive Heart Failure: The Framingham Heart Study", Circulation, 2002, pp. 3068-3072, vol. 106.
Mitnovetski et al., "Extra-Aortic Implantable Counterpulsation Pump in Chronic Heart Failure", Ann. Thorac. Surg., 2008, pp. 2122-2125, vol. 85.
Sales et al., "Understanding the C-Pulse Device and Its Potential to Treat Heart Failure", Curr. Heart Fail. Rep., 2010, pp. 27-34, vol. 7.
Salmons et al. "The Working Capacity of Skeletal Muscle Transformed for Use in a Cardiac Assist Role", Futura Publ Co, 1990, pp. 89-104 (Abstract).
Schulz et al., "Preliminary Results From the C-Pulse Options HF European Multicenter Post-Market Study", Med. Sci. Monit. Basic Res., 2016, pp. 14-19, vol. 22.
Trumble, "A Muscle-Powered Counterpulsation Device for Tether-Free Cardiac Support: Form and Function 1", J. Med. Devices, 2016, pp. 1-2, vol. 10.
Trumble, "Linear muscle power for cardiac support: Current progress and future directions", Basic Appl. Myol., 2009, pp. 35-40 , vol. 19.
Trumble et al., "A muscle-powered energy delivery system and means for chronic in vivo testing", J. Appl. Physiol., 1999, pp. 2106-2114, vol. 86.
Trumble et al., "A permanent prosthesis for converting in situ muscle contractions into hydraulic power for cardiac assist", J. Appl. Physiol., 1997, pp. 1704-1711, vol. 82.
Trumble et al., "Design Improvements and In Vitro Testing of an Implantable Muscle Energy Converter for Powering Pulsatile Cardiac Assist Devices", J Med Devices, 2010, pp. 1-4, vol. 4.
Trumble et al., "Method for measuring long-term function of muscle-powered implants via radiotelemetry", J. Appl. Physiol., 2001, pp. 1977, vol. 90.
Trumble et al., "Muscle-Powered Mechanical Blood Pumps", Science, 2002, vol. 296.
Werner et al., "Pneumatic External Counterpulsation: A New Non-invasive Method to Improve Organ Perfusion", Am. J. Cardiol., 1999, pp. 950-952, vol. 84.

* cited by examiner

MUSCLE-POWERED PULSATION DEVICE FOR LONG-TERM CARDIAC SUPPORT

CROSS REFERENCE TO RELATED APPLICATIONS

This application is the United States national phase of International Application No. PCT/US2018/038181 filed Jun. 19, 2018, and claims the benefit of U.S. Provisional Application Nos. 62/603,984 and 62/604,037, filed Jun. 19, 2017 and Jun. 21, 2017, respectively, the disclosures of each of which hare hereby incorporated in reference in their entireties.

STATEMENT REGARDING FEDERALLY SPONSORED RESEARCH

This invention was made with government support under contract #5 R01 EB019468 awarded by the National Institutes of Health. The government has certain rights in the invention.

BACKGROUND OF THE INVENTION

Field of the Invention

The present disclosure is, generally, directed to a muscle energy converter system and, more particularly, to a muscle-powered pulsation system for long-term cardiac support.

Description of Related Art

Conventional long-term ventricular assist devices (VADs) continue to be extremely problematic due to infections caused by percutaneous drivelines and thrombotic events associated with the use of blood-contacting surfaces. Congestive heart failure (CHF), a progressive condition in which cardiac function deteriorates over time, remains one of the most costly diseases in the industrialized world, both in terms of healthcare dollars and the loss of human life. It is estimated that 26 million people currently suffer from CHF worldwide, including 5.8 million people in the United States where the economic impact exceeds $30 billion per year in medical costs and lost productivity. Further, roughly half of all people who develop CHF die within five years of diagnosis due to the limitations of current long-term treatment strategies. Cardiac transplantation is generally considered to be the best recourse for end-stage CHF patients, but this treatment option is not available to most patients due to a limited donor pool. Pharmacologic therapies can improve heart function in the short term and relieve the symptoms associated with CHF, but are unable to restore and maintain normal heart function over the long term. And despite decades of development work, ventricular assist devices (VADs) are still used mostly as short-term bridges to transplantation due to two persistent limitations: bacterial infection of percutaneous drivelines and thromboembolic complications associated with blood-contacting surfaces.

One method of alleviating these longstanding problems created by drivelines and blood contacting surfaces is to avoid them altogether, by harnessing the body's own endogenous energy stores (e.g., skeletal muscle) and applying this power to the external surface of the heart or ascending aorta. One example of such a device is an implantable muscle energy converter (MEC). The MEC is, in essence, an internal energy transfer mechanism that utilizes electrically stimulated skeletal muscle as an endogenous power source and transmits this energy in hydraulic form. This device exhibits excellent anatomic fit, extreme mechanical durability, and high energy transfer efficiency (>90%) with the capacity to transmit up to 1.25 joules of contractile work per actuation cycle. One such example of an MEC is disclosed in U.S. Pat. No. 6,945,926, issued on Sep. 20, 2005, the disclosure of which is hereby incorporated in its entirety by reference.

The latissimus dorsi muscle (LDM) is especially well-suited for use as the MEC's power source due to its large size, surgical accessibility, proximity to the thoracic cavity, and steady-state work capacity sufficient for long-term cardiac support. Secure muscle-device fixation is achieved using an artificial tendon sewn into the humeral insertion of the LDM, which is then anchored to the actuator arm of the MEC using a patented clamp-and-loop technique. LDM contractions are controlled by a programmable pacemaker-like device (cardiomyostimulator) that coordinates muscle activity with the cardiac cycle. As the actuator arm rotates upward in response to LDM shortening, a rotary cam compresses a metallic spring bellows located directly underneath, ejecting 5 mL of pressurized fluid through the outlet port.

The advantages of this device for long-term circulatory support are significant. By efficiently translating stimulated contractile energy into hydraulic power, the MEC serves to both reduce the risk of infection across the skin and enhance patient quality-of-life by eliminating the need for external hardware components such as extracorporeal battery packs, transmission coils, and percutaneous drivelines. Moreover, muscle-powered VADs are far simpler to maintain and hence are much less expensive in aggregate than traditional blood pumps used for destination therapy, thereby resulting in wider availability, and reduced costs for healthcare providers.

Counterpulsation is a commonly used cardio-therapeutic mechanism that assists left ventricular function by lowering pressure afterloads in the aorta while increasing coronary perfusion. This is typically accomplished with inflatable balloon pumps that displace blood from the aorta during the filling phase of the cardiac cycle. However, unlike conventional intra-aortic balloon pumps (IABPs) that displace blood from the inside of the vessel, extra-aortic balloon pumps (EABP) squeeze the aorta from the outside and preclude secondary complications, such as thromboembolism, by avoiding contact with the blood stream. Results have shown that a 20 mL balloon inflation at the aortic root can effectively counterpulsate the heart and improve patient outcomes. Unfortunately, direct application of the MEC for counterpulsation is not possible since conventional MECs are designed for high-pressure, low-volume (e.g., 5 mL) energy transmission. Thus, there is a need for a mechanism to effectively drive counterpulsation devices, such as EABPs, or other internal pneumatic devices without use of external pneumatics or significantly larger drive units than a typical low volume (e.g., 5 mL) MEC.

SUMMARY OF THE INVENTION

In view of the foregoing, there is a current need for a completely self-contained, non-blood-contacting cardiac assist device for long-term use that would provide an advancement in circulatory support technology. Further, there is a need for an implantable volume amplification mechanism (iVAM) to boost the MEC output volume.

In one example of the present disclosure, a muscle-powered pulsation device for cardiac support may include a muscle energy converter device including a piston arrangement for directing fluid out of an outlet of the muscle energy converter device using energy provided by a patient's muscle, and a hydraulic volume amplification device fluidly connected to the muscle energy converter device. The volume amplification device may include a casing comprising an inlet and an outlet, the inlet in fluid communication with the outlet of the muscle energy converter device, at least one resilient member positioned within an interior cavity defined by the casing, and at least one piston member movably and sealingly positioned within the interior cavity of the casing and operatively connected to the at least one resilient member, the at least one piston member separating the interior cavity into a first chamber and a second chamber.

In another example of the present disclosure, the at least one resilient member may include a pair of bellows. The at least one piston member may include a pair of piston members. A first piston member may be connected to a first bellows and a second piston member may be connected to a second bellows. The at least one piston may include an upper piston member and a lower piston member. The at least one resilient member may be operatively connected to and positioned between the upper piston member and the lower piston member. The volume amplification device may include an inlet port configured to be connected to an outlet port of the muscle energy converter device. The interior cavity of the casing may define a third chamber that is in fluid communication with the muscle energy converter device. The third chamber may be in fluid communication with the first chamber. The first chamber may be fluidly sealed from the second chamber such that fluid cannot pass between the first chamber and the second chamber.

In another example of the present disclosure, a muscle-powered pulsation system may include a muscle energy converter device configured to direct fluid out of an outlet of the muscle energy converter device using energy provided by a patient's muscle, a hydraulic volume amplification device fluidly connected to the muscle energy converter device, and a balloon pump fluidly connected to the volume amplification device. The volume amplification device may be configured to amplify a volume of the fluid directed from the muscle energy converter device to the balloon pump.

In another example of the present disclosure, the balloon pump may include an extra-aortic balloon pump. The balloon pump may include a first plurality of tubes separated from a second plurality of tubes by at least one sidewall. The balloon pump may include two separate sidewalls configured to separate the first plurality of tubes and the second plurality of tubes. The balloon pump may include a sleeve configured to compress ventricles of a patient's heart. A connecting conduit may fluidly connect the volume amplification device and the balloon pump. The volume amplification device may include a casing, at least one resilient member positioned within an interior cavity defined by the casing, and at least one piston member movably positioned within the interior cavity of the casing, the at least one piston member separating the interior cavity into a first chamber and a second chamber. The at least one resilient member may include a pair of bellows. The at least one piston member may include a pair of piston members. A first piston member may be connected to a first bellows and a second piston member may be connected to a second bellows. The at least one piston may include an upper piston member and a lower piston member. The at least one resilient member may be operatively connected to and positioned between the upper piston member and the lower piston member.

In another example of the present disclosure, a method for moving fluid in a patient using a muscle of a patient may include rotating an actuator arm mechanism against a bellows mechanism in a casing when the muscle pulls the actuator arm mechanism, rotating a rotary cam of the actuator arm mechanism against a roller bearing cam follower, forcing fluid out of an outlet port of the casing into a volume amplification device, forcing the fluid against a nested bellow and piston arrangement positioned within the volume amplification device, and forcing a supplemental fluid out of an outlet port of the volume amplification device.

In another example of the present disclosure, the method may further include directing the supplemental fluid from the outlet port of the volume amplification device to a balloon pump. The method may include inflating the balloon pump with the supplemental fluid to compress an aorta of the patient. The balloon pump may be inflated with the supplemental fluid while a heart of the patient is relaxed. The method may include inflating the balloon pump with the supplemental fluid to compress ventricles of the patient. The balloon pump may be inflated with the supplemental fluid during a diastole cycle. The volume amplification module may include a module casing comprising an inlet and an outlet, the inlet in fluid communication with an outlet of the casing, at least one resilient member positioned within an interior cavity defined by the module casing, and at least one piston member movably and sealingly positioned within the interior cavity of the module casing and operatively connected to the at least one resilient member. The at least one piston member may separate the interior cavity into a first chamber and a second chamber.

Further examples will now be described in the following numbered clauses.

Clause 1: A muscle-powered pulsation device for cardiac support, comprising: a muscle energy converter device comprising a piston arrangement for directing fluid out of an outlet of the muscle energy converter device using energy provided by a patient's muscle; and a hydraulic volume amplification device fluidly connected to the muscle energy converter device, the volume amplification device comprising: a casing comprising an inlet and an outlet, the inlet in fluid communication with the outlet of the muscle energy converter device; at least one resilient member positioned within an interior cavity defined by the casing; and at least one piston member movably and sealingly positioned within the interior cavity of the casing and operatively connected to the at least one resilient member, the at least one piston member separating the interior cavity into a first chamber and a second chamber.

Clause 2: The muscle-powered pulsation device as recited in Clause 1, wherein the at least one resilient member comprises a pair of bellows.

Clause 3: The muscle-powered pulsation device as recited in Clause 1 or 2, wherein the at least one piston member comprises a pair of piston members, and wherein a first piston member is connected to a first bellows and a second piston member is connected to a second bellows.

Clause 4: The muscle-powered pulsation device as recited in any of Clauses 1-3, wherein the at least one piston comprises an upper piston member and a lower piston member, and wherein the at least one resilient member is operatively connected to and positioned between the upper piston member and the lower piston member.

Clause 5: The muscle-powered pulsation device as recited in any of Clauses 1-4, wherein the volume amplification device further comprises an inlet port configured to be connected to an outlet port of the muscle energy converter device.

Clause 6: The muscle-powered pulsation device as recited in any of Clauses 1-5, wherein the interior cavity of the casing defines a third chamber that is in fluid communication with the muscle energy converter device.

Clause 7: The muscle-powered pulsation device as recited in Clause 6, wherein the third chamber is in fluid communication with the first chamber.

Clause 8: The muscle-powered pulsation device as recited in any of Clauses 1-7, wherein the first chamber is fluidly sealed from the second chamber such that fluid cannot pass between the first chamber and the second chamber.

Clause 9: A muscle-powered pulsation system, comprising: a muscle energy converter device configured to direct fluid out of an outlet of the muscle energy converter device using energy provided by a patient's muscle; a hydraulic volume amplification device fluidly connected to the muscle energy converter device; and a balloon pump fluidly connected to the volume amplification device, wherein the volume amplification device is configured to amplify a volume of the fluid directed from the muscle energy converter device to the balloon pump.

Clause 10: The muscle-powered pulsation system as recited in Clause 9, wherein the balloon pump comprises an extra-aortic balloon pump.

Clause 11: The muscle-powered pulsation system as recited in Clause 9 or 10, wherein the balloon pump comprises a first plurality of tubes separated from a second plurality of tubes by at least one sidewall.

Clause 12: The muscle-powered pulsation system as recited in Clause 11, wherein the balloon pump includes two separate sidewalls configured to separate the first plurality of tubes and the second plurality of tubes.

Clause 13: The muscle-powered pulsation system as recited in any of Clauses 9-12, wherein the balloon pump comprises a sleeve configured to compress ventricles of a patient's heart.

Clause 14: The muscle-powered pulsation system as recited in any of Clauses 9-13, further comprising a connecting conduit fluidly connecting the volume amplification device and the balloon pump.

Clause 15: The muscle-powered pulsation system as recited in any of Clauses 9-14, wherein the volume amplification device comprises: a casing; at least one resilient member positioned within an interior cavity defined by the casing; and at least one piston member movably positioned within the interior cavity of the casing, the at least one piston member separating the interior cavity into a first chamber and a second chamber.

Clause 16: The muscle-powered pulsation system as recited in Clause 15, wherein the at least one resilient member comprises a pair of bellows.

Clause 17: The muscle-powered pulsation system as recited in Clause 15 or 16, wherein the at least one piston member comprises a pair of piston members, and wherein a first piston member is connected to a first bellows and a second piston member is connected to a second bellows.

Clause 18: The muscle-powered pulsation system as recited in any of Clauses 15-17, wherein the at least one piston comprises an upper piston member and a lower piston member, and wherein the at least one resilient member is operatively connected to and positioned between the upper piston member and the lower piston member.

Clause 19: A method for moving fluid in a patient using a muscle of a patient, comprising: rotating an actuator arm mechanism against a bellows mechanism in a casing when the muscle pulls the actuator arm mechanism; rotating a rotary cam of the actuator arm mechanism against a roller bearing cam follower; forcing fluid out of an outlet port of the casing into a volume amplification device; forcing the fluid against a nested bellow and piston arrangement positioned within the volume amplification device; and forcing a supplemental fluid out of an outlet port of the volume amplification device.

Clause 20: The method recited in Clause 19, further comprising directing the supplemental fluid from the outlet port of the volume amplification device to a balloon pump.

Clause 21: The method recited in Clause 19 or 20, further comprising inflating the balloon pump with the supplemental fluid to compress an aorta of the patient.

Clause 22: The method recited in Clause 21, wherein the balloon pump is inflated with the supplemental fluid while a heart of the patient is relaxed.

Clause 23: The method recited in Clause 19 or 20, further comprising inflating the balloon pump with the supplemental fluid to compress ventricles of the patient.

Clause 24: The method recited in Clause 23, wherein the balloon pump is inflated with the supplemental fluid during a diastole cycle.

Clause 25: The method recited in any of Clauses 19-24, wherein the volume amplification module comprises: a module casing comprising an inlet and an outlet, the inlet in fluid communication with an outlet of the casing; at least one resilient member positioned within an interior cavity defined by the module casing; and at least one piston member movably and sealingly positioned within the interior cavity of the module casing and operatively connected to the at least one resilient member, the at least one piston member separating the interior cavity into a first chamber and a second chamber.

Clause 26: The muscle-powered pulsation device as recited in any of Clauses 1-8, wherein the at least one resilient member comprises a pair of nested bellows.

Clause 27: The muscle-powered pulsation system as recited in any of Clauses 15-18, wherein the at least one resilient member comprises a pair of nested bellows.

Clause 28: The method recited in Clause 25, wherein the at least one resilient member comprises a pair of nested bellows.

Further details and advantages will be understood from the following detailed description read in conjunction with the accompanying drawings.

DESCRIPTION OF THE DISCLOSURE

Figure 1:
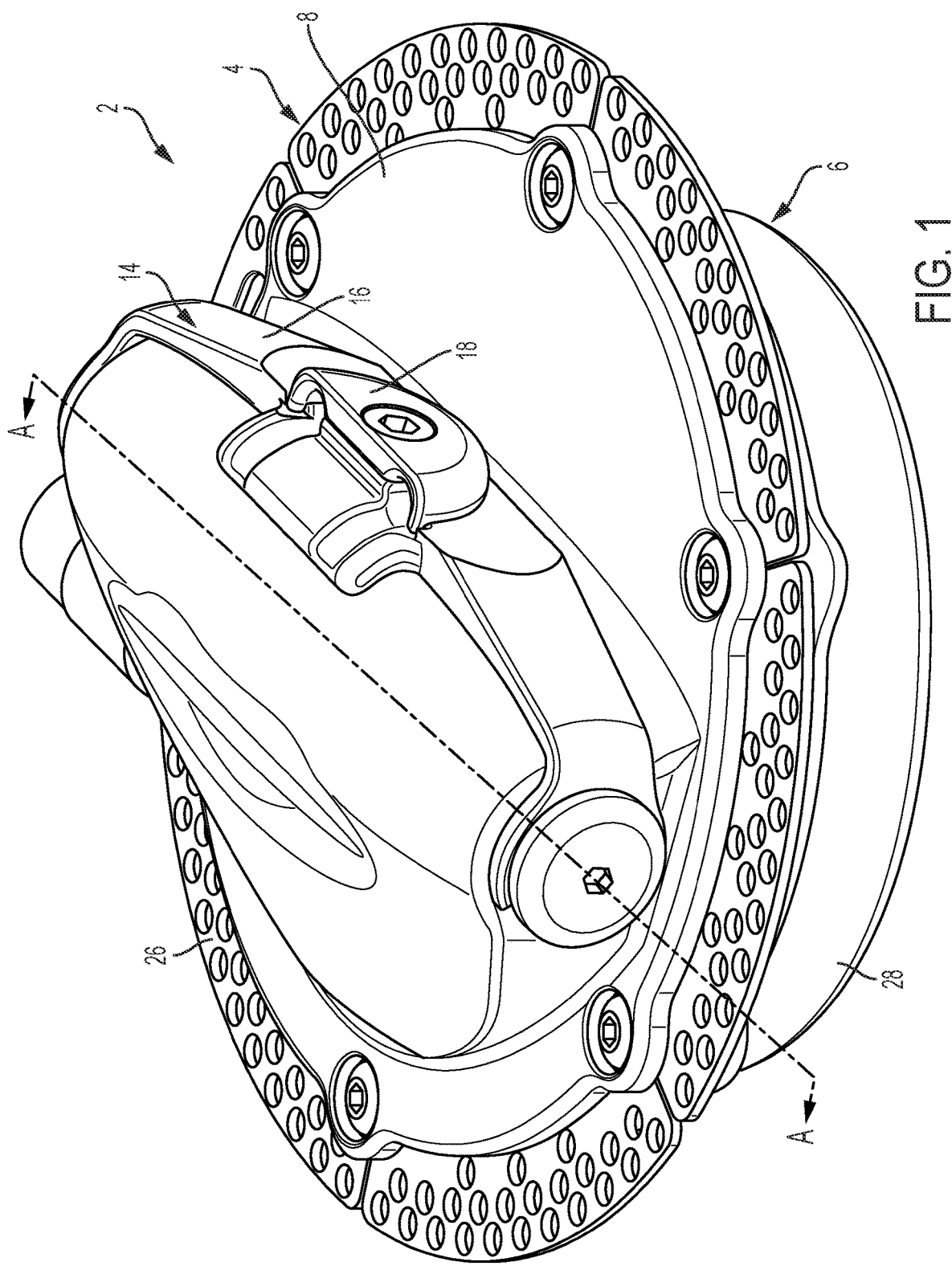
FIG. 1 is a top perspective view of a muscle energy convertor system according to an example of the present disclosure.
Figure 2:
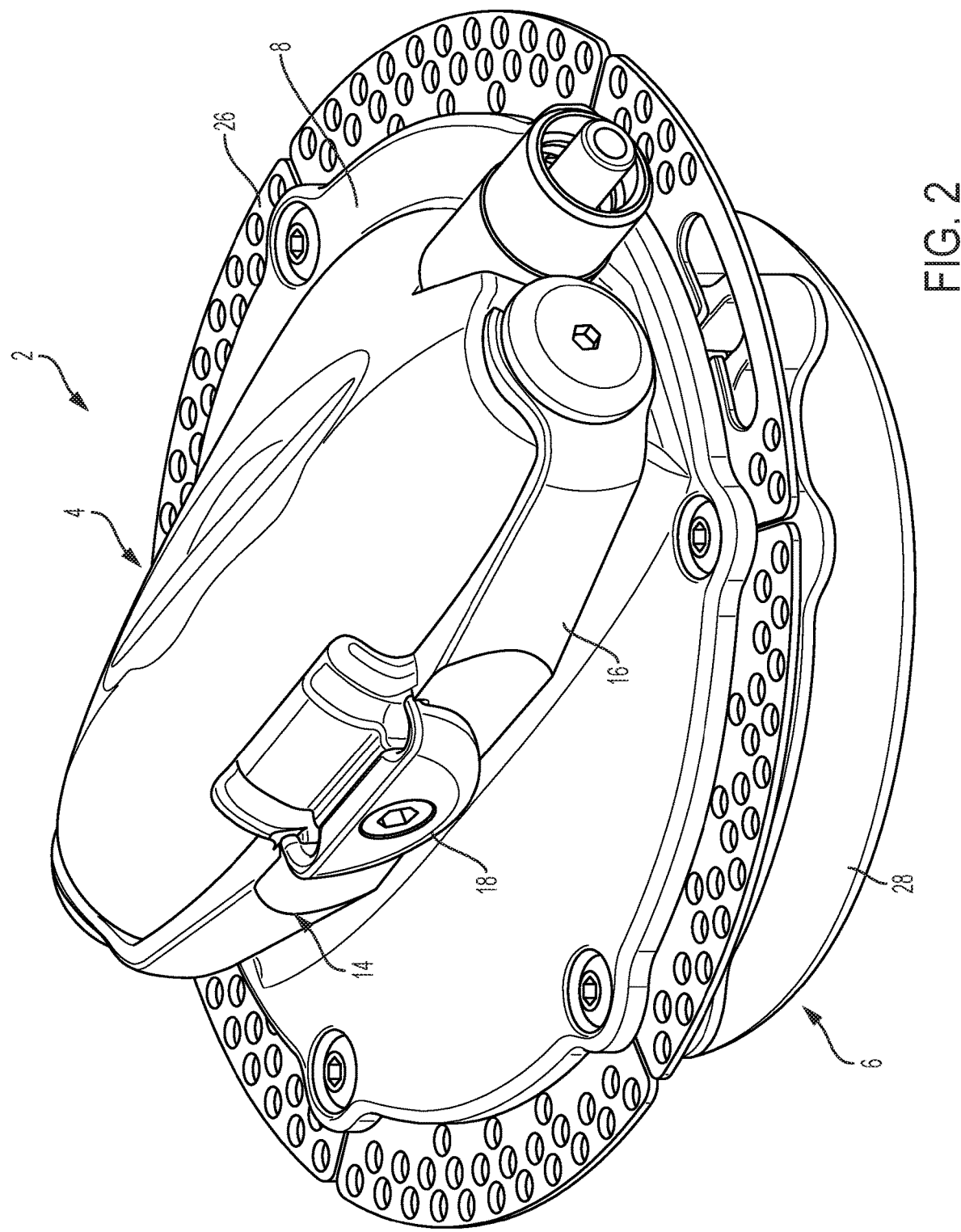
FIG. 2 is a top perspective view of the muscle energy convertor system of FIG. 1.
Figure 3:
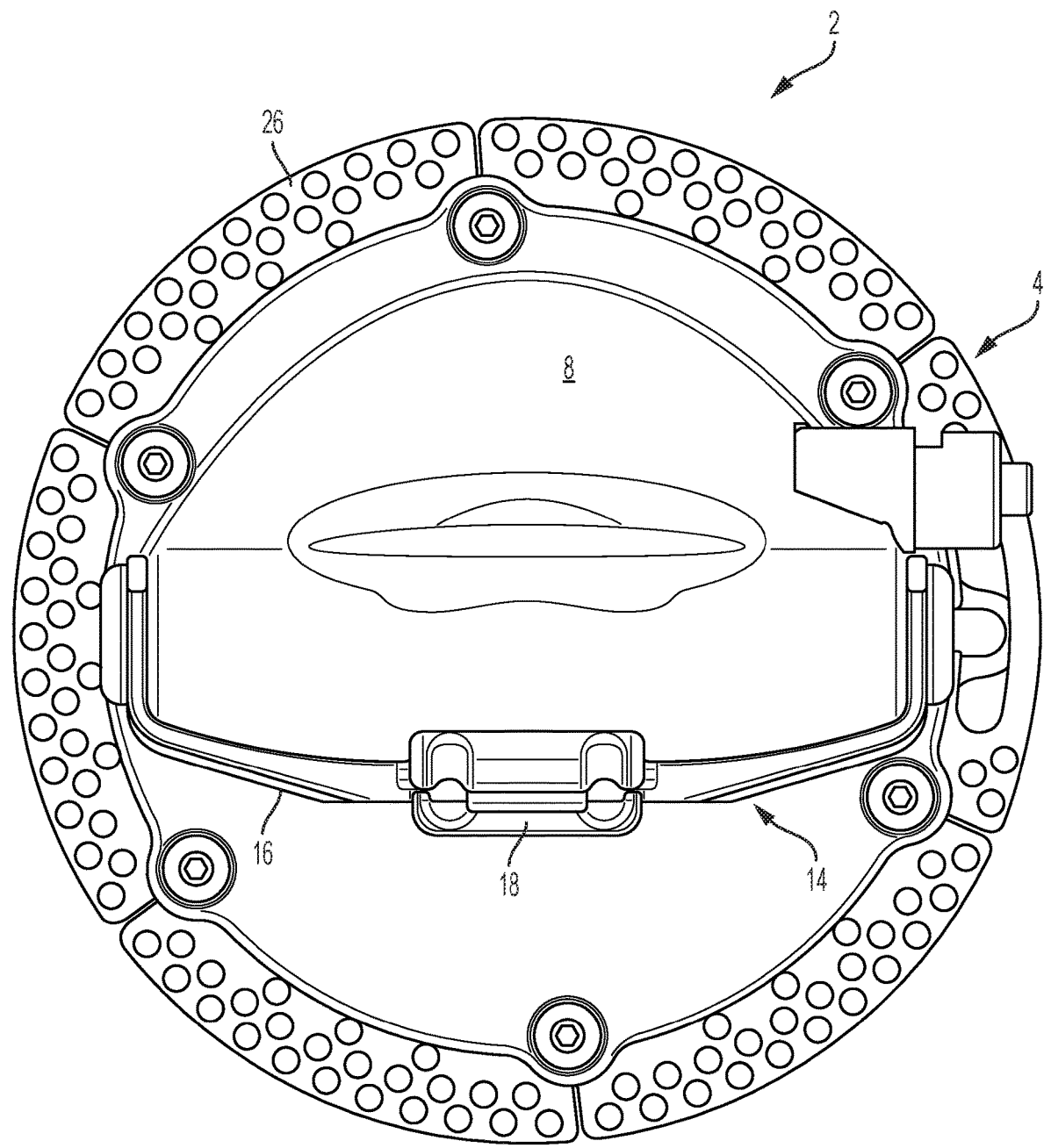
FIG. 3 is a top view of the muscle energy convertor system of FIG. 1.
Figure 4:
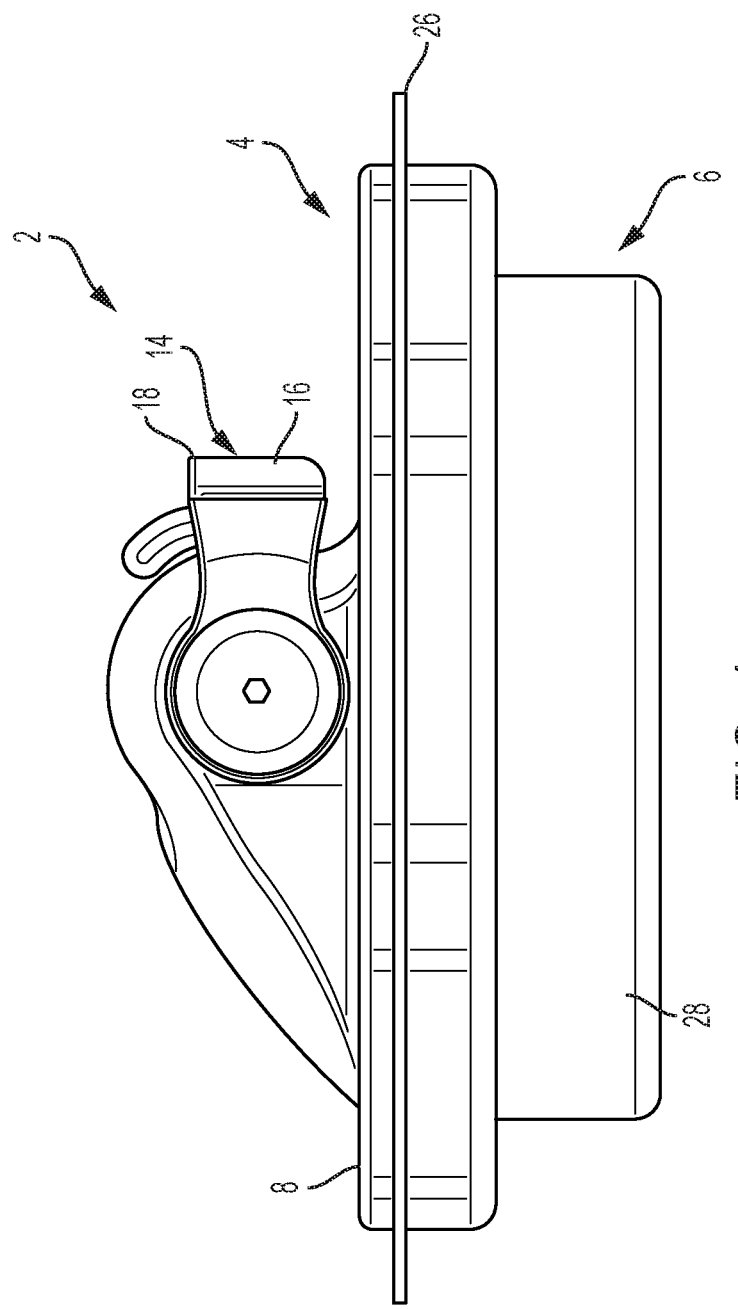
FIG. 4 is a side view of the muscle energy convertor system of FIG. 1.
Figure 5:
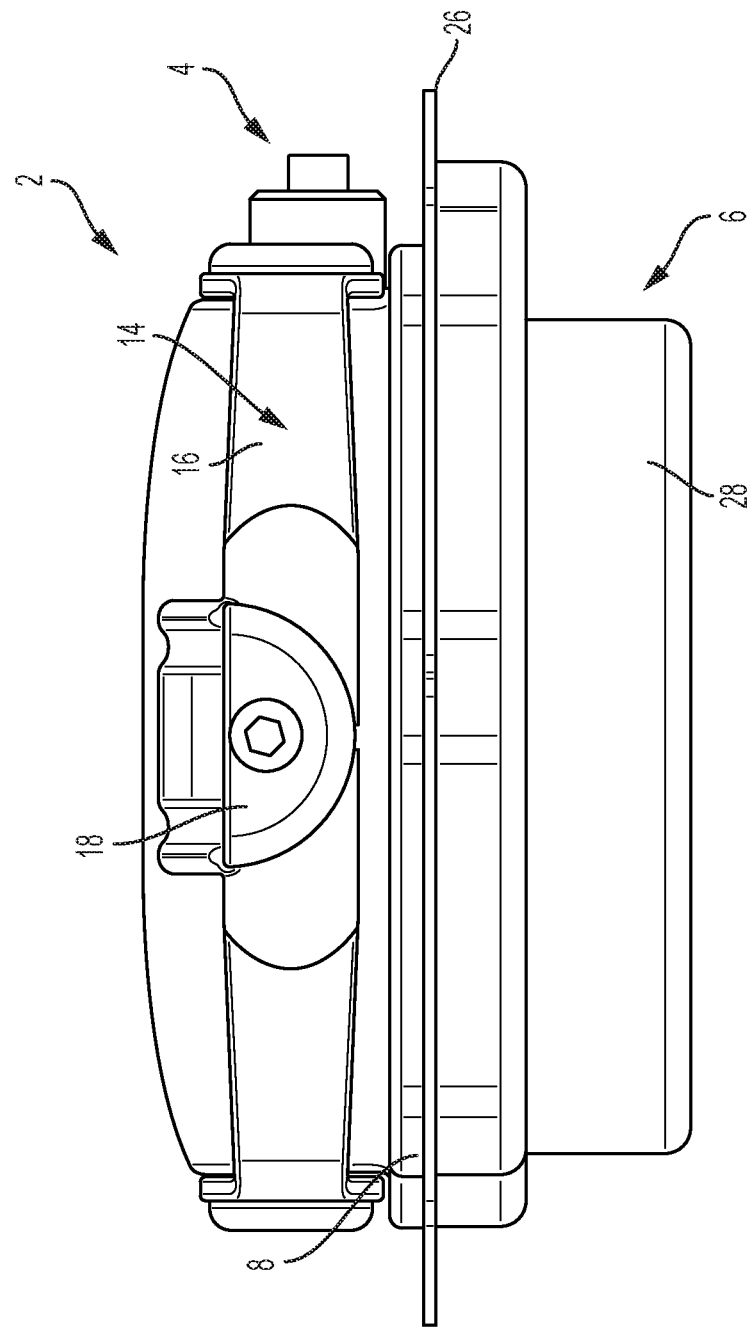
FIG. 5 is a side view of the muscle energy convertor system of FIG. 1.
Figure 6:
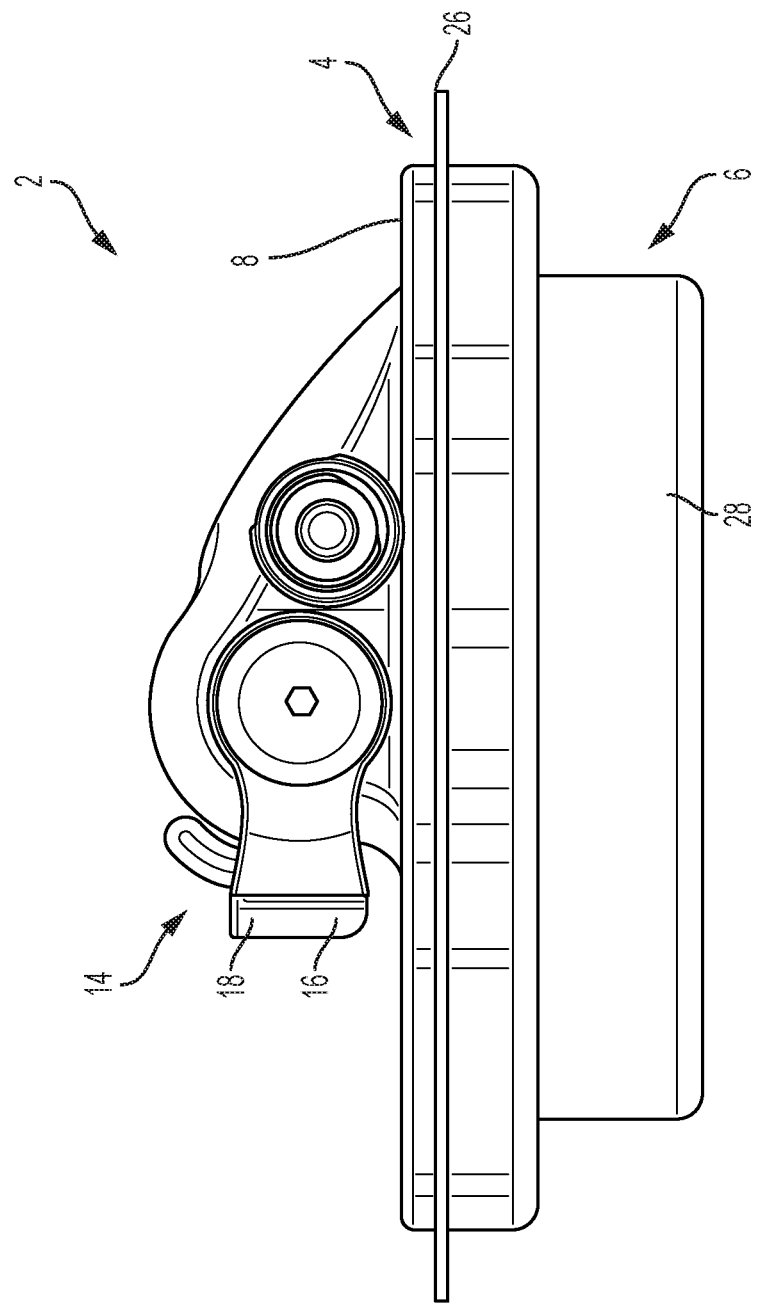
FIG. 6 is a side view of the muscle energy convertor system of FIG. 1.
Figure 7:
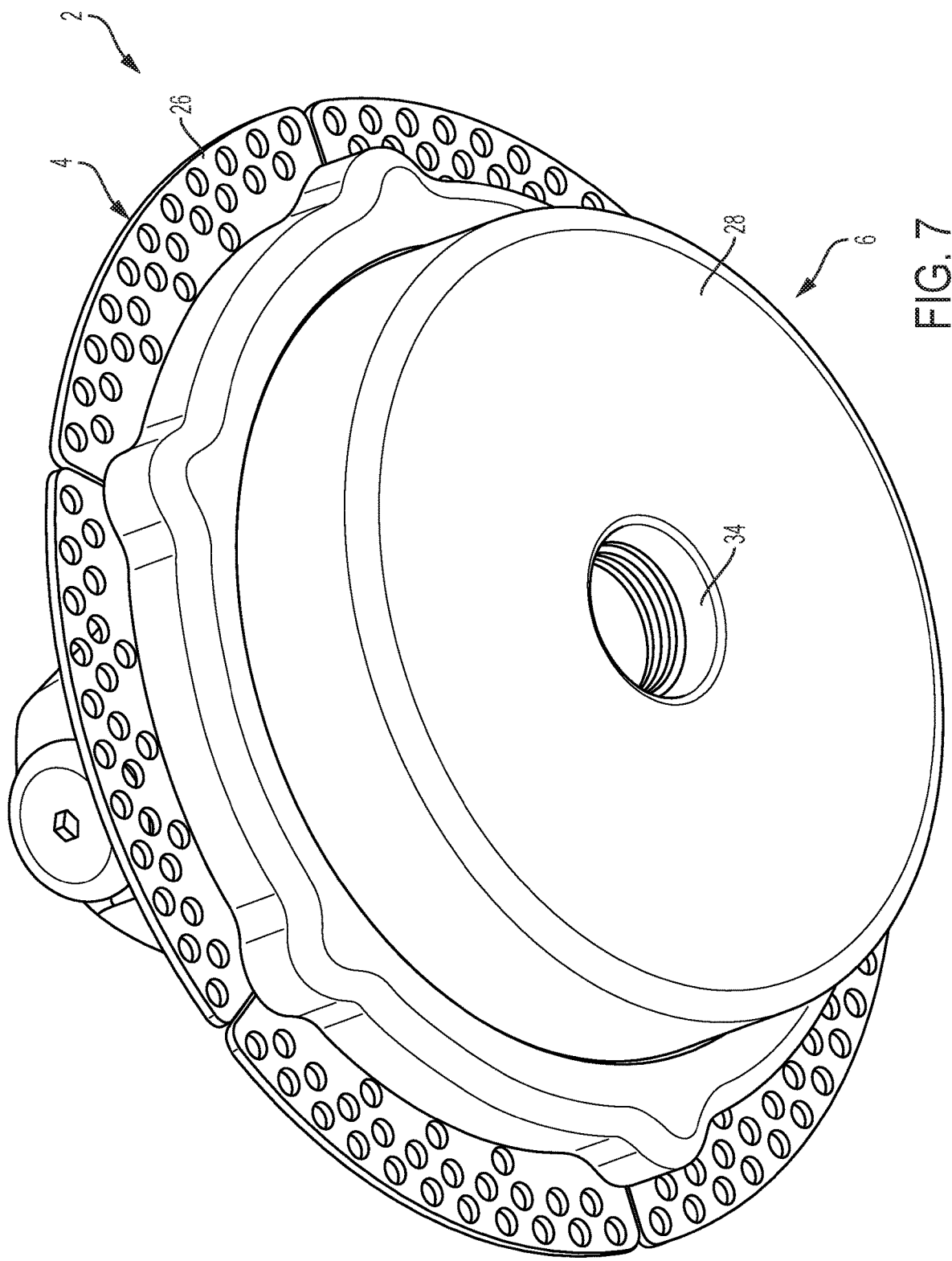
FIG. 7 is a bottom perspective view of the muscle energy convertor system of FIG. 1.
Figure 8:
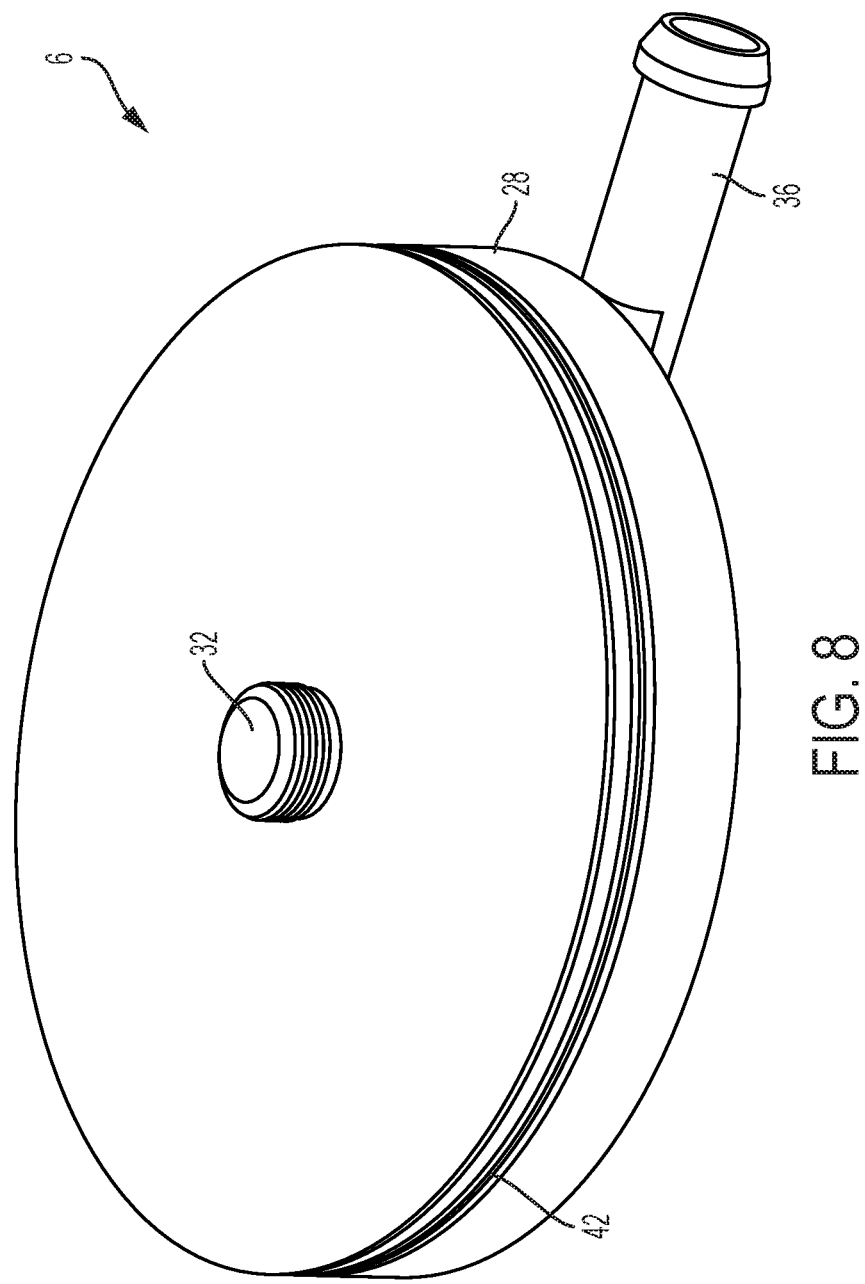
FIG. 8 is a top perspective view of a volume amplification module according to one example of the present disclosure.
Figure 9:
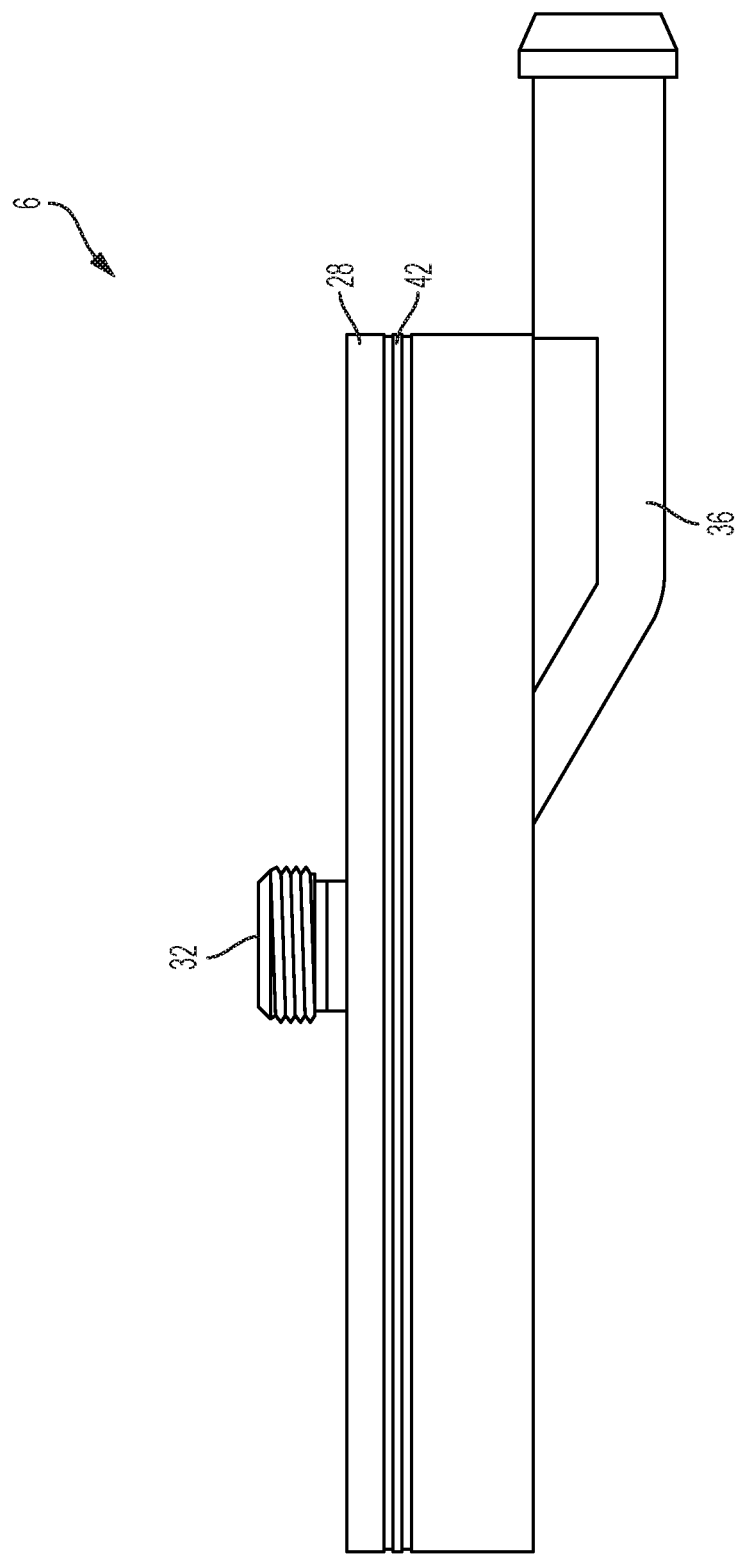
FIG. 9 is a side view of the volume amplification module of FIG. 8.

For purposes of the description hereinafter, spatial orientation terms, as used, shall relate to the referenced embodiment as it is oriented in the accompanying drawings, figures, or otherwise described in the following detailed description. However, it is to be understood that the embodiments described hereinafter may assume many alternative variations and configurations. It is also to be understood that the specific components, devices, features, and operational sequences illustrated in the accompanying drawings, figures, or otherwise described herein are simply exemplary and should not be considered as limiting.

The present disclosure is directed to, generally, a muscle energy converter system and, more particularly, to a muscle-powered pulsation system for long-term cardiac support. With reference to FIGS. 1-17, the muscle energy convertor system 2 (hereinafter referred to as "system 2", also referred to as a muscle-powered pulsation system) including a muscle energy converter device 4 (also referred to as a muscle-powered pulsation device) and a volume amplification module 6 is shown and described. The system 2 may be implantable within a patient and may be configured to increase the volume of fluid provided to a pulsation pump used to assist in cardiac support.

With reference to FIGS. 1-6, the muscle energy converter device 4 is shown and described. The muscle energy converter device 4 may be similar to the muscle energy converter device disclosed in U.S. Pat. No. 6,945,926, issued Sep. 20, 2005, the disclosure of which is hereby incorporated in its entirety by reference. The muscle energy converter device 4 may include a casing 8 having a fluid outlet port 10. The muscle energy converter device 4 may also include a bellows mechanism 12 (also referred to as a piston arrangement) adapted to contain fluid. The muscle energy converter device 4 may also include an actuator arm mechanism 14 configured to be attached to a tendon of a muscle of the patient, which moves against the bellows mechanism 12 when the muscle pulls the actuator arm mechanism 14 and forces fluid out of the fluid outlet port 10. The actuator arm mechanism 14 may be operatively connected to the casing 8.

In one example, the actuator arm mechanism 14 includes an actuator arm 16, the actuator arm 16 having an attachment portion 18 configured to attach to a tendon of a muscle of the patient. The actuator arm mechanism 14 may include a bushing mechanism that engages the actuator arm 16 and the casing 8, and guides the actuator arm 16. The bushing mechanism may include a spring-loaded lip seal and a bushing attached to the casing 8 and engaged with the actuator arm 16. The actuator arm 16 may be moved between a resting position and a compressed position. The bushing may be configured to guide the actuator arm 16 and restore the actuator arm 16 to the resting position once the actuator arm 16 has been moved to the compressed position.

Figure 12A:
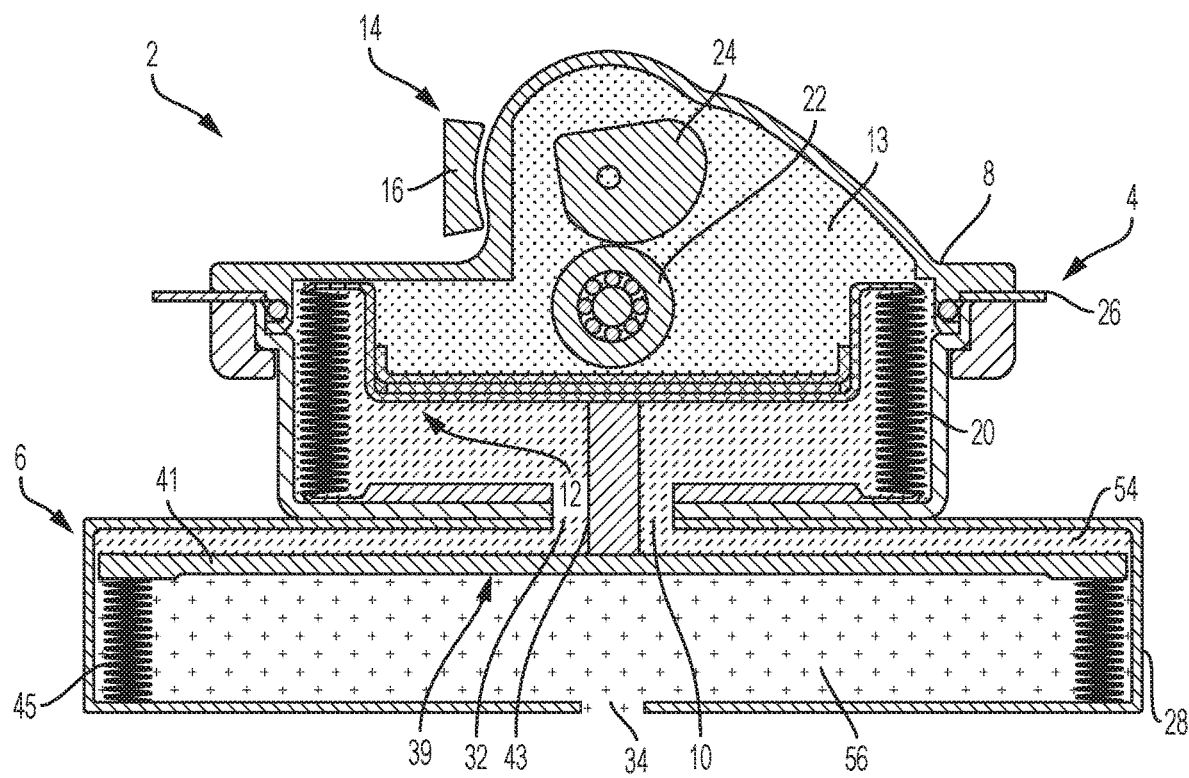
FIG. 12A is a cross-sectional view of the muscle energy convertor system of FIG. 1 along line A-A.

With reference to FIG. 12A, the bellows mechanism 12 may include a bellows 20 disposed in the casing 8 that is adapted to contain a fluid, such as air or liquid. In one example, a roller bearing/cam follower mechanism 22 may also be positioned within the casing 8 and may be in contact with the bellows 20. An inner chamber 13 may be defined above the bellows mechanism 12. The bellows 20 may be positioned between the fluid outlet port 10 and the roller bearing/cam follower mechanism 22. The actuator arm mechanism 14 may also include a rotary cam 24 disposed on the actuator arm 16, which pushes against the roller bearing/cam follower mechanism 22 when the actuator arm 16 is rotated from the resting position to the compressed position. As the rotary cam 24 is pressed against the roller bearing/cam follower mechanism 22, the bellows 20 are compressed so as to force the fluid in the casing 8 out through the fluid outlet port 10 when the muscle pulls the actuator arm 16. Since fluid is pumped by the bellows 20, the fluid can be cycled in compression while simultaneously providing a return force to reset the muscle energy converter device 4 between contractions.

As shown in FIG. 1, a rim 26 extends around the circumference of the casing 8. The rim 26 may be made of a thin perforated metal. The rim 26 may be used to attach the system 2 to a patient's chest wall or rib cage. The rim 26 may be segmented and thin enough to bend by hand to permit a surgeon to adjust the contour of the rim 26 as needed according to different chest wall dimensions in different patients. Once inserted on the patient's chest wall or rib cage, scar tissue may infiltrate and encapsulate the rim 26 to anchor the system 2. The system 2 may be configured to sit across the patient's rib cage with the muscle energy converter device 4 resting above the ribs and the volume amplification module 6 passing through the ribs so that the volume amplification module 6 is positioned below (i.e., completely within the chest cavity). Optimum anatomic fit may be accomplished by stacking the two devices one against the other so that the volume amplification module 6 of the system 2 is able to sit comfortably against an inner lining of the chest wall with minimal lung displacement. The system 2 not only provides a low-profile transthoracic fit, but also reduces device weight and minimizes energy loss.

With reference to FIGS. 1, 7-10, 12A, and 12B, several examples of the volume amplification module 6 are shown and described in detail. The volume amplification module 6 may be configured to increase the volume output of the muscle energy converter device 4 to a balloon pump or other positive displacement pump device. In one example, the volume amplification module 6 may be hydraulic. The volume amplification module 6 may include a casing 28 that defines an interior cavity 30. The casing 28 may be substantially cylindrical and may have an outer diameter that is smaller than an outer diameter of the rim 26. The volume amplification module 6 may be made of the same material as the muscle energy converter device 4. In one example, the volume amplification module 6 and the muscle energy converter device 4 are made of steel. It is contemplated, however, that any material suitable for implantation in a patient may be used for the muscle energy converter device 4 and the volume amplification module 6.

Figure 10:
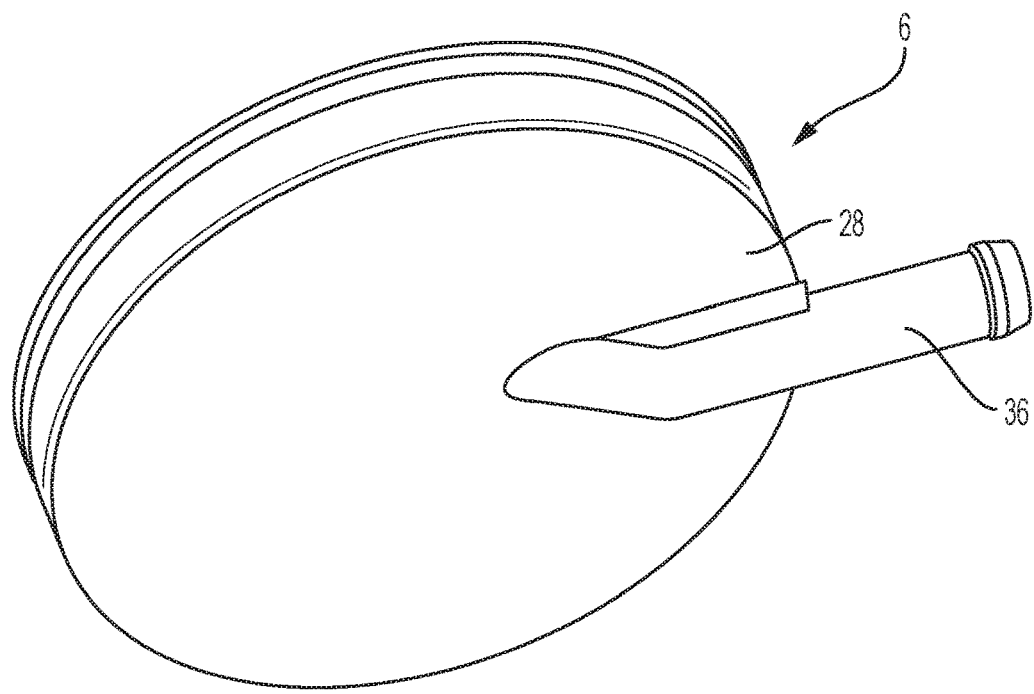
FIG. 10 is a bottom perspective view of the volume amplification module of FIG. 8.
Figure 11:
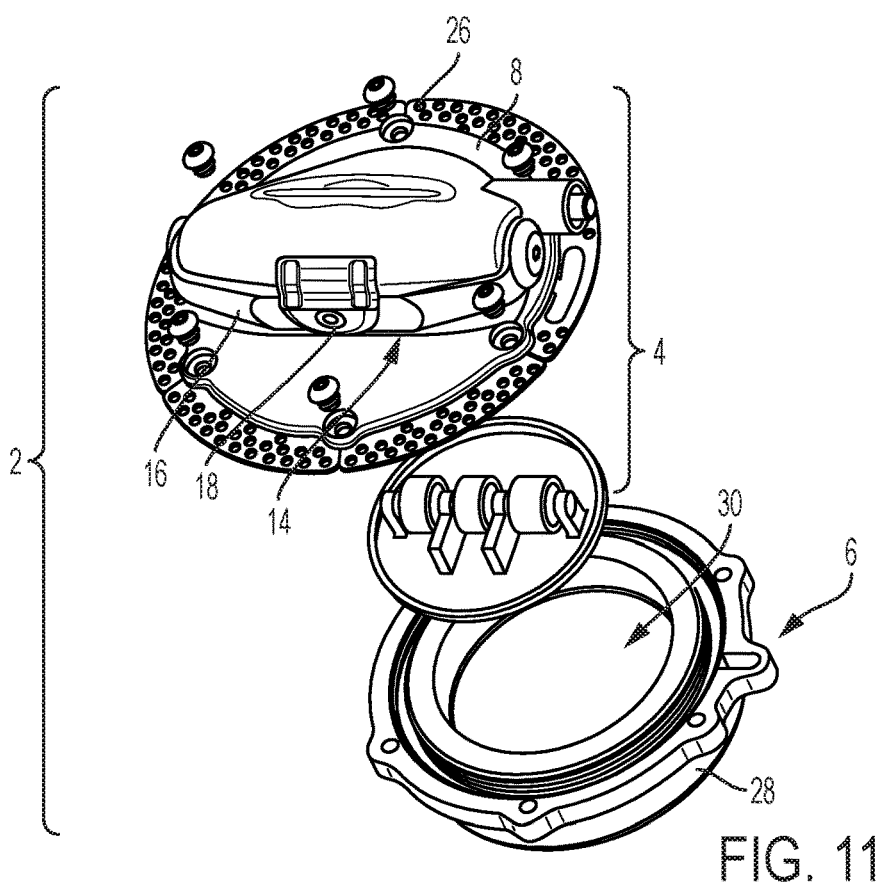
FIG. 11 is an assembly view of the muscle energy convertor system of FIG. 1.
Figure 12B:
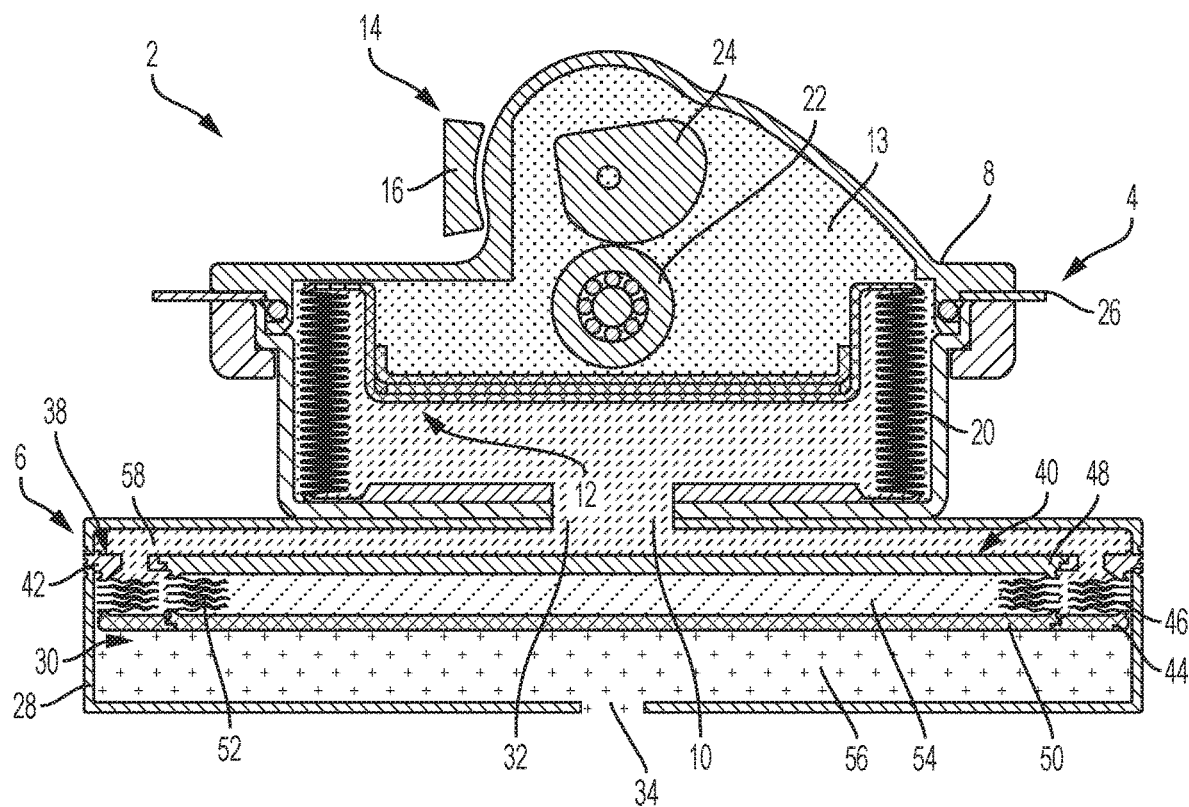
FIG. 12B is a cross-sectional view of an example of a muscle energy convertor system according to the present disclosure.

As shown in FIG. 12B, the volume amplification module 6 may include an inlet port 32 defined in an upper portion of the casing 28 and an outlet port 34 defined in a lower portion of the casing 28. The inlet port 32 may be in fluid communication with the fluid outlet port 10 of the muscle energy converter device 4. In one example, the inlet port 32 may be threadedly connected to the fluid outlet port 10 of the muscle energy converter device 4. Fluid directed out of the fluid outlet port 10 of the muscle energy converter device 4 is directed into the volume amplification module 6 via the inlet port 32. Fluid is directed out of the interior cavity 30 of the casing 28 through the outlet port 34. As shown in FIG. 10, a conduit 36 extending from the lower surface of the casing 28 may direct fluid from the outlet port 34 to a balloon pump or a pneumatic pump device.

With reference to FIG. 12A, in one example of the present disclosure, a volume amplification arrangement may be provided within the interior cavity 30 of the casing 28 that is configured to amplify the volume of fluid that is directed from the muscle energy converter device 4 to the balloon pump or pneumatic pump device. The volume amplification arrangement may include a piston arrangement 39. The piston arrangement 39 may include a piston 41 and a piston rod 43. The piston 41 may be sealingly and movably positioned within the interior cavity 30 of the casing 28. The piston rod 43 is operatively connected to the bellows mechanism 12 of the muscle energy converter device 4 on one end thereof and to the piston 41 on an opposing end thereof. The piston rod 43 may extend from the bellows mechanism 12 to the piston 41 through the outlet 10 of the muscle energy converter device 4 and the inlet 32 of the volume amplification module 6. Since the piston 41 is connected to the bellows mechanism 12 via the piston rod 43, the piston 41 may be configured to move in unison with the bellows mechanism 12. The piston 41 may sealingly engage the inner surface of the casing 28 so as to divide the interior cavity 28 into a first chamber 54 and a second chamber 56. The first and second chambers 54, 56 may be configured to hold a volume of fluid. In this configuration, the first chamber 54 is pneumatic and may receive a volume of gas from the muscle energy converter device 4 via the inlet 32 of the volume amplification module 6. A volume of fluid may be directed out of the volume amplification module 6 from the second chamber 56 via the outlet 34. The volume amplification arrangement may also include a resilient member 45 positioned within the interior cavity 30 of the casing 28. The resilient member 45 may be positioned beneath the piston 41 in the second chamber 56 of the interior cavity 30. The resilient member 45 may be compressible upon receiving pressure from the piston 41. Upon release of the pressure, the resilient member 45 may be configured to return to an uncompressed state. In one example, the resilient member 45 is a bellows. It is to be understood that a resilient member may be any component capable of moving between a compressed or deformed configuration and an uncompressed or undeformed configuration.

With continued reference to FIG. 12A, operation of the volume amplification module 6 is described. The upper left ribcage is an ideal location for the system 2 implantation due to its proximity to both the latissimus dorsi muscle (LDM) insertion point and the ascending aorta. Comfortable implantation and secure fixation may be achieved by placing the system 2 across a transthoracic window created by resection of a 6.5 cm portion of one rib. The rim 26 may be anchored to the adjacent ribs with wire suture while the bottom two-thirds of the system 2 will fit across and within the chest wall (see FIG. 14). The muscle energy converter device 4 may be oriented so that the direction of the actuator arm rotation aligns with the direction of the LDM shortening for maximum energy transfer efficiency. Inside the chest wall, the orientation of the outlet port 10 will be arranged to minimize the flow path and hence optimize fluid transfer efficiency between the muscle energy converter device 4 and the volume amplification module 6 and a balloon pump. The strength of fixation sites linking the device, muscle and chest wall may improve and ultimately stabilize over time as fibrous tissue in-growth proceeds during the initial 2-4 weeks of device implantation.

After the muscle energy converter device 4 has been activated, the bellows mechanism 12 is pressed in a direction towards the volume amplification module 6. Due to the connection of the piston 41 to the bellows mechanism 12 via the piston rod 43, the piston 41 will be pushed towards the outlet 34 due to the movement of the bellows mechanism 12. As the piston 41 is moved in a direction towards the outlet 34, the resilient member 45 is compressed by the piston 41. Due to the compression of the piston 41, a volume of fluid held within the second chamber 56 is directed out of the outlet 34 of the volume amplification module 6 to be directed into a balloon pump or other positive displacement pump device. This fluid directed out of the second chamber 56 is directed to the balloon pump or other positive displacement pump device via the conduit 36 to assist in creating a pumping function for the balloon pump or other positive displacement pump device.

With reference to FIG. 12B, in one example of the present disclosure, a volume amplification arrangement may be provided within the interior cavity 30 of the casing 28 that is configured to amplify the volume of fluid that is directed from the muscle energy converter device 4 to the balloon pump or positive displacement pump device. The volume amplification arrangement may include a first piston arrangement 38 and a second piston arrangement 40. In one example, the first piston arrangement 38 has a greater diameter than the second piston arrangement 40. In one example, the second piston arrangement 40 may be nested within the first piston arrangement 38. The first piston arrangement 40 may be sealingly held within the casing 28.

In one example, the first piston arrangement 38 may include an upper piston member 42, a lower piston member 44, and a resilient member 46 positioned between the upper and lower piston members 42, 44. In one example, the resilient member 46 is operatively connected to both the upper and lower piston members 42, 44. In one example, the resilient member 46 is a bellows member. It is to be understood, however, that any suitable resilient member may be used with the first piston arrangement 38, such as a spring. Using the resilient member 46, the upper and lower piston members 42, 44 are configured to move towards and away with one another according to the fluid pressure exerted against the piston members 42, 44. In one example, the second piston arrangement 40 may include an upper piston member 48, a lower piston member 50, and a resilient member 52 positioned between the upper and lower piston members 48, 50. In one example, the resilient member 52 is operatively connected to both the upper and lower piston members 48, 50. In one example, the resilient member 52 is a bellows member. It is to be understood, however, that any suitable resilient member may be used with the second piston arrangement 40, such as a spring. Using the resilient member 52, the upper and lower piston members 48, 50 are configured to move towards and away with one another according to the fluid pressure exerted against the piston members 48, 50.

With reference to FIG. 12B, the upper piston member 48 of the second piston arrangement 40 may rest on the upper piston member 42 of the first piston arrangement 38. In a similar fashion, the lower piston member 50 of the second piston arrangement 40 may rest on the lower piston member 44 of the first piston arrangement 38. The lower piston members 44, 50 may separate the interior cavity 30 into a first chamber 54 defined above the lower piston members 44, 50 and a second chamber 56 defined below the lower piston members 44, 50. The lower piston members 44, 50 may sealingly engage one another and the casing 28 so that fluid is not permitted to move between the first and second chambers 54, 56. The second chamber 56 may be in fluid communication with the outlet port 34 and the conduit 36. The upper piston members 42, 48 may separate the first chamber 54 and a third chamber 58 defined in the interior cavity 30 of the casing 28. The third chamber 58 may be defined above the upper piston members 42, 48. The third chamber 58 may be in fluid communication with the inlet port 32. An aperture defined in the upper piston member 42 of the first piston arrangement 38 permits fluid to be directed between the third chamber 58 and the first chamber 54.

With continued reference to FIG. 12B, operation of the volume amplification module 6 is described. After a volume of fluid has been directed out of the muscle energy converter device 4, the volume of fluid is directed into the third chamber 58 of the volume amplification module 6 via the inlet port 32 where it enters into the space between the resilient members 46, 52. As the fluid is directed into this expandable space, the fluid pressure pushes downwardly against the lower piston members 44, 50 of the first and second piston arrangements 38, 40. As the lower piston members 44, 50 are pushed downwardly, the resilient members 46, 52 are extended to move with the lower piston members 44, 50 and the sealed pneumatic chamber 54 expands to create a negative gas pressure that contributes to active filling of chamber 56 during muscle relaxation. As the lower piston members 44, 50 are pushed downwardly, a volume of fluid held within the second chamber 56 is pushed out of the second chamber 56 through the outlet port 34. This fluid directed out of the second chamber 56 is directed to the balloon pump or hydraulic pump device via the conduit 36 to assist in creating a pumping function for the balloon pump or hydraulic pump device.

Using the volume amplification module 6 with the muscle energy converter device 4, the volume of fluid delivered to the balloon pump or hydraulic pump device can be increased up to four times the volume of fluid that would normally be delivered by the muscle energy converter device 4 alone. The volume amplification of the volume amplification module 6 may be achieved by using an area difference between the two piston arrangements 38, 40. In one example, the 5 mL of pressurized fluid ejected from the muscle energy converter device 4 is amplified by four times to eject 20 mL of fluid towards the balloon pump.

Similar to a hydraulic machine with high energy transfer efficiency requirements, the system 2 is configured to minimize turbulence and pressure gradients throughout the fluid flow path through the system 2. To accomplish this, the system 2 may include an enlarged flow path between the muscle energy converter device 4 and the volume amplification module 6 that lowers hydraulic resistance therebetween, a centered outlet port 10 in the muscle energy converter 4 that minimizes turbulence between the muscle energy converter device 4 and the volume amplification module 6, and a stacked configuration that shortens the fluid travel distance between the muscle energy converter device 4 and the volume amplification module 6. In one example, the flow profile of the system was investigated using computational fluid dynamics analyses. One-eighth of the system 2 was reconstructed for expedited flow analyses within the selected reduced volume. Boundary pressure and inlet and outlet flow rates were set to 1 atm and 19.9 mL/s, respectively, for water ($\rho_{H2O}$=0.98 g/mL) against Titanium bellows ($K_n$=41) operating at body temperature. The results of the investigation showed a laminar flow throughout the fluid path with an improved streamline density, flow trajectory, and pressure drop profile. The pressure drop across the entire fluid path was just 0.0238 psi, which was small enough to be neglected with respect to overall energy loss calculations (<0.2%).

The system 2 may be designed to operate at contractile force and velocity levels compatible with the functional capacity of fully conditioned human muscles, which, at peak sustainable power production, generates roughly 95N force and shortens at a rate of 11 cm/s.[8] To confirm the patient's muscle's ability to reliably power the system 2, actuation force requirements of the system 2 may be calculated to correspond with those created by extreme hypertensive loading conditions (i.e., 155 mmHg mean diastolic pressure).

As described above, activation of the system 2 begins with lifting the actuator arm 16 of the muscle energy converter device 4, which may be designed with a 5N preload force to allow the actuator arm 16 to overcome the passive resting tension of a fully-trained muscle. Rapid rotation of the actuator arm 16 (for example, ≤250 msec) is needed in order to complete inflation of the balloon pump during the first half of the diastolic period, but rapid return of the actuator arm 16 to the rest position is equally important since balloon pump deflation must be complete before the onset of cardiac systole. Hence, the distribution of actuator arm forces in both forward- and return-stroke directions is an important design consideration. These forces may be adjusted via manipulation of two dynamic components internal to the system 2 including the spring constants of the resilient members 20, 45, 46, 52 and partial vacuum pressures within the chambers 13, 54. Material, thickness, inner and outer diameter, number of diaphragms, and the contour of the convolutions determine the spring constant of the resilient members 46, 52, which may be installed at slightly compressed states and tuned to produce both preload return force (provided by resilient members in the muscle energy converter device 4) and an opposing force in the forward-stroke direction (resilient members 46, 52 in the volume amplification module 6). Partial vacuum spaces created within the system 2 during the volume amplification module 6 contraction store energy within the device and add force in the return-stroke direction, which helps to rapidly deflate the balloon pump and reset the actuator arm 16 between contractions. Using force vectors and a force balance equation, it has been determined that, in one example of the system 2, a mean contractile force of 54.1N over the course of the stroke and a maximum contractile force of 83.9N at the end of the stroke of the resilient arm 16 will be required by the muscle to actuate the system 2.

The force generated by the LDM applied over a muscle shortening length (d) can be directly translated to an amount of energy generated by the muscle with each contraction. The work produced by the LDM (W), which calculates to be 1.175 J, may be used both to inflate and deflate the balloon pump to a pressure of 3 psi (155 mmHg) over the course of one complete actuation cycle. One complete cycle is the sum of two phases: 1) the forward-stroke where the output fluid enters and inflates the balloon pump and 2) the return-stroke where the fluid exits the balloon pump. A fraction of input work W is stored among four different components while the remainder is delivered to the balloon pump during the forward-stroke. During the return-stroke, the stored energies work to pull the fluid back into the system 2. The work generated by the LDM (W) is distributed among four different 'storage' sites (W1: work stored in the muscle energy converter device vacuum space; W2: work stored in the muscle energy converter resilient member; W3: work stored in the volume amplification module resilient members; and W4: work stored in the volume amplification module vacuum space) and the balloon pump (W5: work delivered to the balloon pump)

As described above, system actuation begins with lifting the actuator arm 16. As the actuator arm 16 lifts, the rotary cam 24 underneath pushes down the roller bearing/cam follower mechanism 22 and the vacuum space in the muscle energy converter device casing 8 expands, creating a more negative gauge pressure within. With increasing volume and decreasing pressure, the air pocket temporarily stores 0.055 J of work (W1) in a form of potential energy that is later used to pull the roller bearing/cam follower mechanism 22 back up during the return-stroke. As the roller bearing/cam follower mechanism 22 lowers and compresses the resilient member in the muscle energy converter device during the forward-stroke, the resilient member stores, for example, 0.124 J of energy (W2). The volume amplification module resilient members 46, 52 contribute 0.066 J of energy (W3) to the forward-stroke as it expands from its initially installed compressed state as fluid is expelled from the volume amplification module 6. The expanding resilient members 46, 52 will push down the lower piston members 44, 50 and increase the volume of the volume amplification module vacuum space 54, lowering the negative pressure within. This air pocket may store 0.648 J of potential energy (W4), which helps to retract the fluid from the balloon pump with muscle relaxation. The remainder of the input energy, W5 (for example, 0.414 J), will be delivered to the balloon pump in the form of a 20 mL volume displacement against 155 mmHg afterload pressure. Since a patient's muscle, such as the LDM, of average mass can be trained to generate 95N under peak sustainable power output conditions, this muscle is a viable power source for the system 2.

Figure 13:
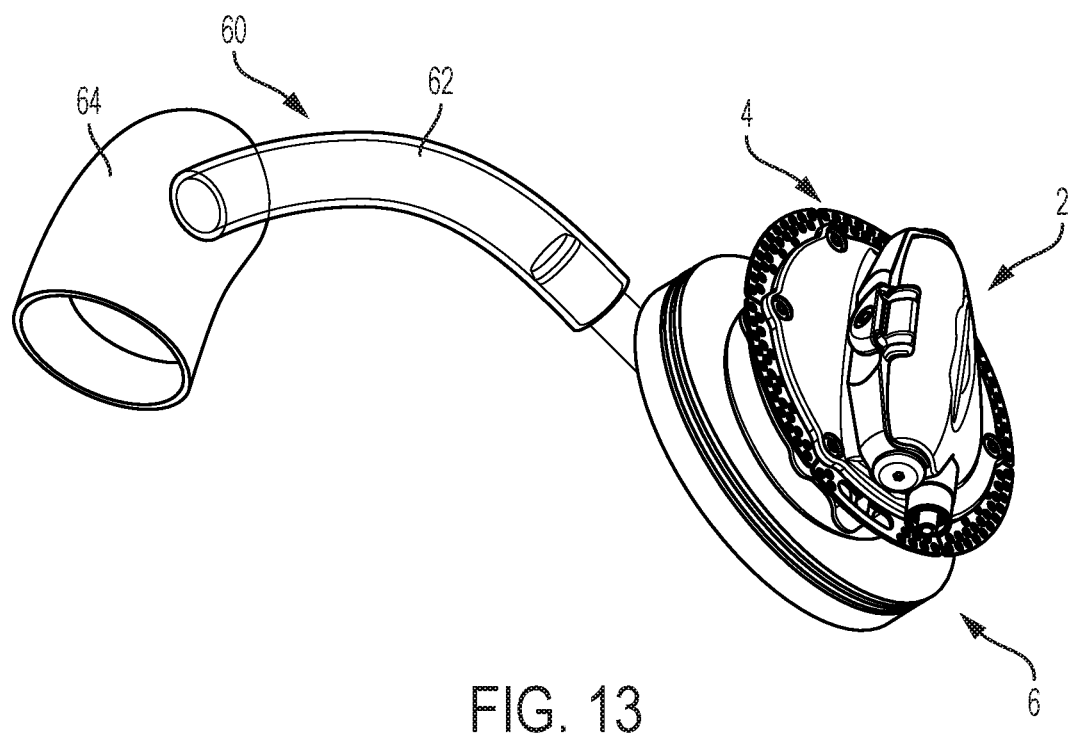
FIG. 13 is a perspective view of the muscle energy convertor system of FIG. 1 operatively connected to a balloon pump according to an example of the present disclosure.
Figure 14:
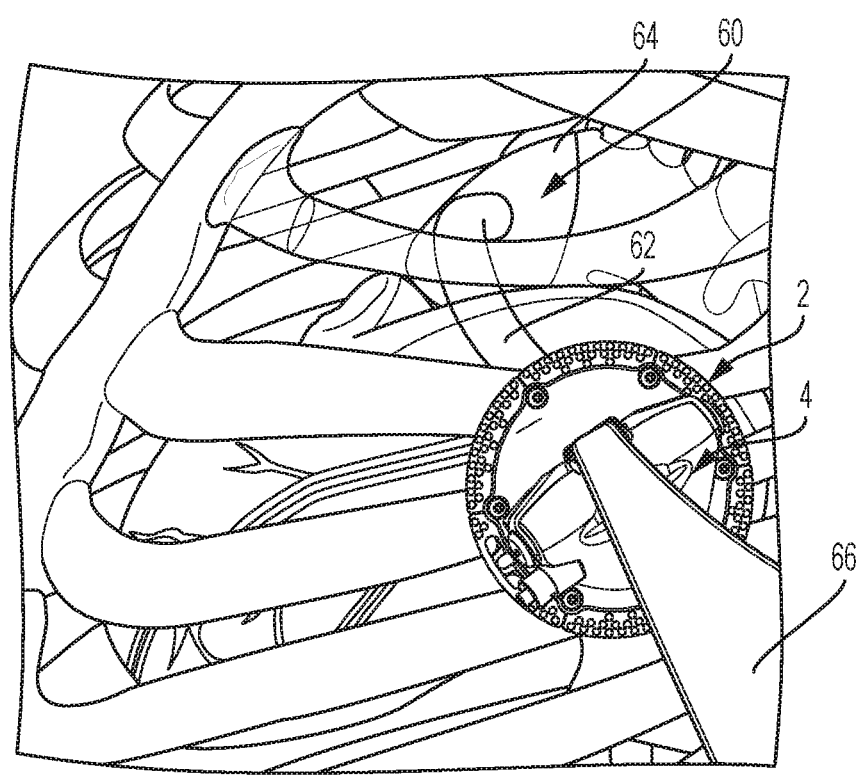
FIG. 14 is a perspective view of the muscle energy convertor system and balloon pump of FIG. 13 operatively connected to an aorta of a patient.

With reference to FIGS. 13 and 14, the system 2 is shown in use with a balloon pump. The system's 2 potential to drive pulsatile blood pumps extends to any form of hydraulic device designed to squeeze or otherwise manipulate a patient's heart or aorta, preferably from the outside. As shown in FIG. 13, the system 2 may be fluidly connected to the balloon pump 60 to provide a pumping function for cardiac support in a patient. The balloon pump 60 may include a fluid conduit 62 and a cuff 64. The fluid conduit 62 may be fit onto the conduit 36 of the volume amplification module 6, so that the fluid directed out of the conduit 36 by the volume amplification module 6 is directed into the balloon pump 60 and, more particularly, into the cuff 64. In one example, the balloon pump 60 may be an extra-aortic balloon pump configured to be positioned on or wrapped about a patient's aorta. As fluid is directed from the volume amplification module 6 to the balloon pump 60, the balloon pump 60 fills with fluid and expands against the aorta to increase pressure against the aorta. The pressure against the aorta assists in moving blood through the aorta to increase the cardiac support for the patient. With reference to FIG. 14, the system 2 is shown attached to the patient's rib cage or chest wall and the balloon pump 60 has been positioned on the patient's aorta. The patient's muscle 66 has also been operatively connected to the muscle energy converter device 4 to initiate operation of the system 2. By using the balloon pump 60 to provide cardiac support, the aorta is squeezed externally by the balloon pump, which avoids blood contact within the patient. In one example, the balloon pump 60 may be inflated while the patient's heart is relaxed so as to direct blood to the patient's heart and push the blood out of the patient's aorta. As the patient's blood begins to pump, the balloon pump 60 is deflated and the fluid held within the balloon pump 60 is directed back into the volume amplification module 6.

Figure 15:
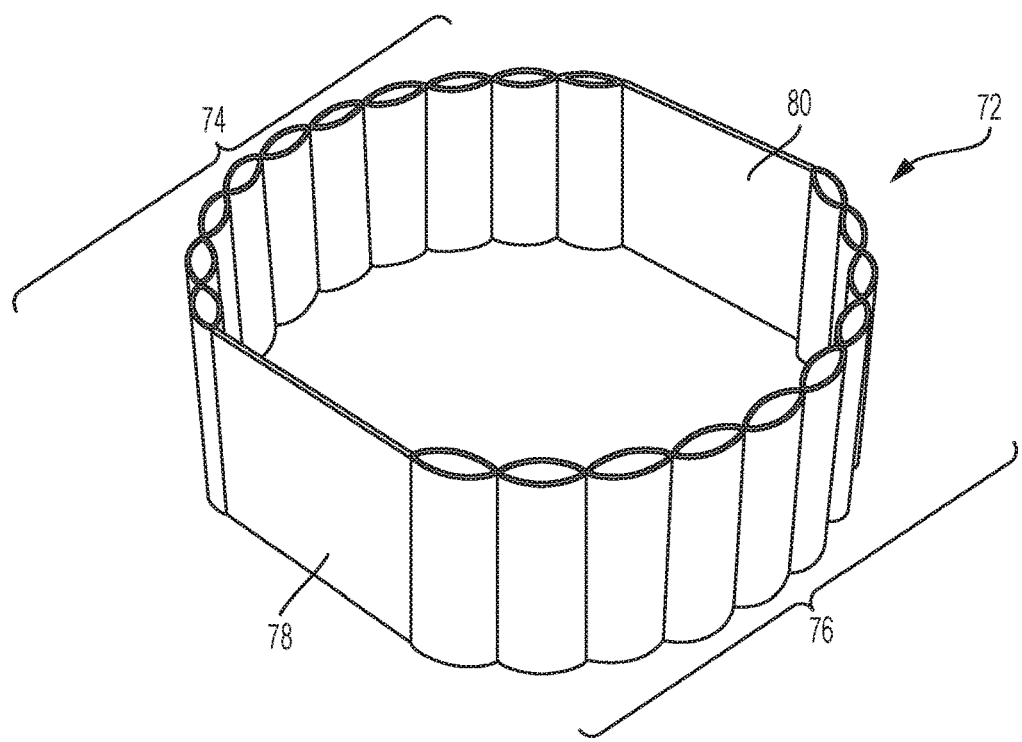
FIG. 15 is a perspective view of a balloon pump according to an example of the present disclosure.
Figure 16:
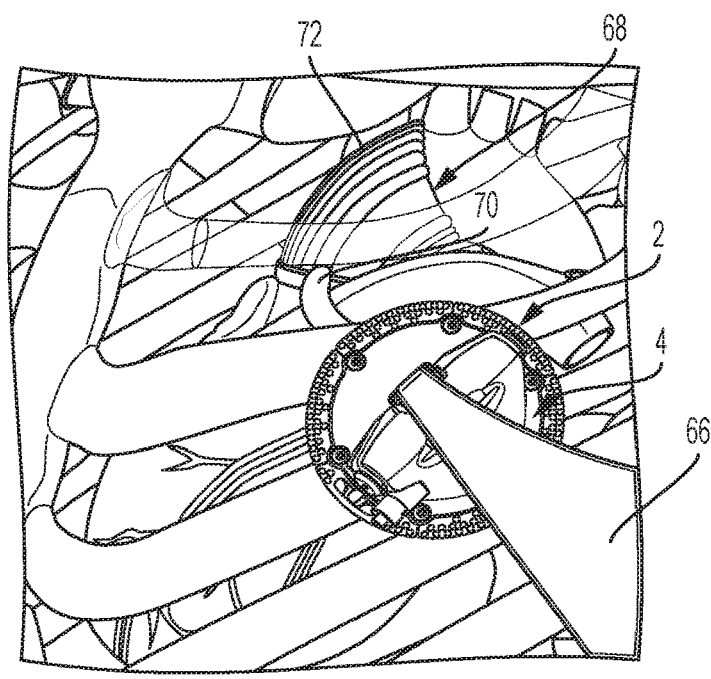
FIG. 16 is a perspective view of the muscle energy convertor system of FIG. 1 and the balloon pump of FIG. 15 operatively connected to an aorta of a patient.

With reference to FIGS. 15 and 16, another example of a balloon pump 68 is shown and described. Similar to the balloon pump 60 described above, the balloon pump 68 is configured to be connected to the system 2 and positioned on or wrapped about an aorta of the patient. The balloon pump 68 includes a fluid conduit 70 configured to be connected to the conduit 36 of the volume amplification module 6 and a cuff 72. The cuff 72 includes a first plurality of tubes 74 and a second plurality of tubes 76. The plurality of tubes 74, 76 are generally formed in an arcuate pattern to wrap around the patient's aorta. The plurality of tubes 74, 76 are separated from one another by a sidewall 78, 80 on each end thereof. The sidewalls 78, 80 are substantially planar and do not have an arcuate shape. The balloon pump 68 may be designed to squeeze the exterior of the ascending aorta and displace 20 mL of blood from the aortic root during diastole. The advantage of this balloon pump 68 over conventional balloon pumps is that the balloon pump 68 can perform this function with a fluid input of only 5 mL, which can come directly from the muscle energy converter device 4 without volume amplification. This is accomplished by leveraging the properties of tubing arrays that contract and expand circumferentially when filled and emptied.

When fluid enters an empty array of thin-walled tubes in conventional balloon pumps, the thin-walled tubes transition from a flat cross sectional configuration to a circular one. The effect of this change is that the effective widths of the tubes decrease. When these tubes are connected side-by-side in a circular fashion, the effect of this transformation becomes readily apparent. When the tubes in the circular array are fully inflated they form a perimeter of length nd, where n is the number of tubes in the array and d is the diameter of each individual tube. When fluid is removed, each tube collapses flat so that their effective width increases from their inflated diameter to roughly one-half their inflated circumference. Thus, each tubular element expands sideways by $\pi/2$ or 57% with deflation and the circumference of the circular array enlarges to $\pi nd/2$. In essence then, each tube acts as a hydraulic actuator in that when fluid fills the device each tube pulls its adjacent attachments toward the center of its longitudinal axis.

One key design element not accounted for by this simple compression scheme, however, is the structure of the aorta itself. Because the ascending aorta is a substantially cylindrical thick-walled vessel, a compression force applied uniformly around the circumference would preferentially increase circumferential hoop stress within the vessel wall.

Under these conditions the tissue layers of the aortic wall (adventitia, smooth muscle layer, and endothelium), would absorb the applied circumferential force until finally buckling under the strain, damaging the aortic wall in the process. To avoid this problem, conventional balloon pumps must be modified to redirect the primary compression force away from the vessel walls and toward the center of the lumen. One way to accomplish this is to position the pair of thin, inelastic polymer sidewalls 78, 80 opposite one another in the array as shown in FIG. 15. In so doing, the contractile force of the tubes 74, 76 will draw the sidewalls 78, 80 towards one another, resulting in a bi-directional displacement that gently compresses the aorta without generating potentially damaging hoop stresses within the aortic wall. In one example, a 20 mL compression of the ascending aorta (OD=3.3 cm) can be accomplished in this way using a split array of 20 thin-walled tubes (OD=2.6 mm, ID=2.2 mm) just 3.5 cm in length.

Figure 17:
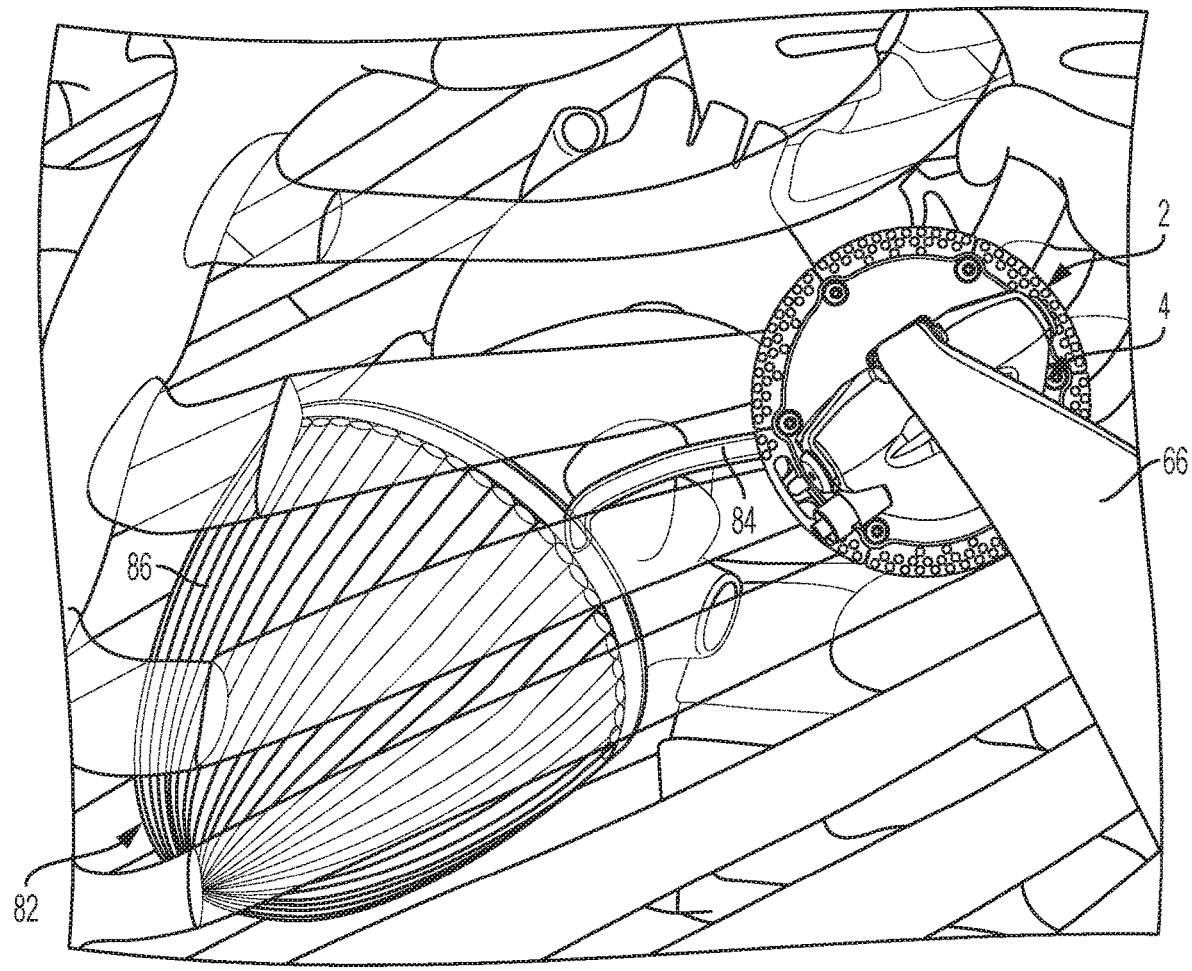
FIG. 17 is a perspective view of the muscle energy convertor system of FIG. 1 and a balloon pump according to an example of the present disclosure operatively connected to ventricles of a patient.

With reference to FIG. 17, in another example of the present disclosure, another balloon pump 82 is used in connection with the system 2. The balloon pump 82 shown in this example includes a fluid conduit 84 and a sleeve 86. The balloon pump 82 is configured to be connected to the system 2 and positioned on or wrapped around the ventricles of the patient's heart. The fluid conduit 84 may be fluidly connected to the conduit 36 of the volume amplification module 6. Fluid delivered from the volume amplification module 6 may be used to inflate the tubes of the sleeve 86 to apply pressure to the ventricles of the patient's heart. The thin-walled polymer tubes may form a soft hydraulic sleeve that covers and compresses the ventricles from the outside. Unlike counterpulsation devices like the balloon pumps 64, 68 that act during diastole, this balloon pump 82 can operate in synchrony with left ventricular ejection. The difference in systolic perimeter nd and diastolic perimeter πnd/2 results in a maximum perimeter change of 36% with inflation, which leads to enclosed volume changes as high as 60% at any given tube length. Fifty 0.15 centimeter wide tubes in an 8 centimeter tall half-prolate spheroid shape amplifies volume by five times, which leads to 100 mL and 25 mL of volume displacements from the muscle energy converter device 4 with and without a volume amplification module 6, respectively. The volume amplification ratio becomes larger as the number of tubes used in the balloon pump 82 increases.

A complete system may include the muscle energy converter device 4, the volume amplification module 6, a fluid conduit 62, and a balloon pump 60. Grade-9 Titanium alloy (Ti-3AL-2.5V) may be used for the system 2 build due to its superior biocompatibility and weldability. The excellent corrosion resistance and high fusibility of this material combine to form a robust weld between the components of the system 2, which is essential for device durability. Sterile deionized water is the energy transmission fluid of choice due to its high specific heat capacity, low density and low viscosity, which make the system less susceptible to temperature changes, turbulent flow, and energy losses over the course of device actuation. An implantable plastic material with high biocompatibility and flexibility such as Polyurethane, Silicone, or PVC, designed to withstand pressurized fluid delivery over millions of cycles, would all be suitable for the fluid conduit 62 and balloon pumps 60. The tubing may be secured on both the volume amplification module 6 and balloon pump 60 ends with implant-grade stainless steel band clips.

The system 2, once implanted, may be expected to function reliably for long-term, if not permanent, use. Bellows height, width, effective area, convolution profile, and stroke length must all be carefully tuned to create appropriate volume amplification in a limited space while minimizing bellows flexion stress. The current bellows design of the system 2 successfully amplifies fluid volume displacement while incorporating the minimum bellows stroke lengths possible in this design space. According to the FEA, the life expectancy of the system bellows exceed 450 million and 10 billion cycles, respectively, which exceeds the fatigue limit of Titanium alloy ($10^7$ cycles) as per ASTM. Therefore, the current system bellows design is rated as "fatigue-free" for an infinite life span. Other internal components, including seals, camshaft and needle bearings, may also be designed for extreme wear and biochemical resistance.

Dynamic testing of the system 2 may be conducted on a bench to confirm proper system function and assess overall mechanical reliability. Muscular actuation may be simulated via a programmable linear actuator. The actuator, which may contain a microprocessor, servo amplifier, memory module, high capacity roller thrust bearing, and encoder, may attach to the muscle energy convertor device 4 via a metal chain to simulate the pull of the LDM while allowing the actuator arm 16 to reset without assistance from the linear actuator return stroke mechanism (as is the case with muscular actuation in which the LDM actively shortens to empty the muscle energy converter device 4 and passively stretches as the muscle energy converter device 4 fills between contractions). Miniature force and displacement transducers may be fixed to the actuator arm 16 to monitor actuation dynamics and calculate total 'contractile' energy used to actuate the system 2. Motor speed and piston/muscle energy converter device coupling dynamics may be programmed to replicate LDM actuation profiles, the primary components being a 22 millimeter draw over a 250 millisecond 'contraction' period. Cycle rates may be varied from 30 to 120 beats/min to measure changes in energy transfer efficiency and establish an upper limit on device cycle frequency. The muscle energy converter device 4 may communicate with the balloon pump via a fluid conduit identical to the internal driveline that will be used in subsequent implant trials. The volume amplification module 6 will attach to a silicone replica of the ascending aorta via a fluid conduit made to empty into a mock circulatory system adjusted to provide mean afterload pressures ranging from 80 to 180 mmHg. The system 2 hydraulic power transmission profile may be monitored using an in-line flow probe and a pressure transducer stationed along the driveline. These waveforms may be used to quantify system coupling dynamics, measure energy transfer efficiency, and determine the mechanical reliability of the actuation scheme. System optimization may result from changes in driveline dimensions and attachment schemes.

While several examples of a system and method for using the system were shown in the accompanying figures and described in detail hereinabove, other aspects will be apparent to, and readily made by, those skilled in the art without departing from the scope and spirit of the disclosure. Accordingly, the foregoing description is intended to be illustrative rather than restrictive. The invention described hereinabove is defined by the appended claims and all changes to the invention that fall within the meaning and range of equivalency of the claims are to be embraced within their scope.

The invention claimed is:

1. A muscle-powered pulsation device for cardiac support, comprising:

a muscle energy converter device comprising a piston arrangement for directing fluid out of an outlet of the muscle energy converter device using energy provided by a patient's muscle; and a hydraulic volume amplification module fluidly connected to the outlet of the muscle energy converter device, the volume amplification module comprising:
- a casing comprising an inlet and an outlet, the inlet in fluid communication with the outlet of the muscle energy converter device;
- at least one resilient member positioned within an interior cavity defined by the casing; and
- at least one piston member movably and sealingly positioned within the interior cavity of the casing between the inlet and the outlet, and operatively connected to the at least one resilient member, the at least one piston member separating the interior cavity into a first chamber and a second chamber and, wherein when the at least one piston member is pneumatically driven by motion of a volume of fluid through the inlet of the casing, and the at least one piston member displaces a larger volume of fluid in the second chamber through the outlet of the casing.

2. The muscle-powered pulsation device as recited in claim 1, wherein the at least one resilient member comprises at least one bellows.

3. The muscle-powered pulsation device as recited in claim 2,
wherein the at least one piston member comprises a pair of piston members, and
wherein a first piston member is connected to a first bellows and a second piston member is connected to a second bellows.

4. The muscle-powered pulsation device as recited in claim 1,
wherein the at least one piston comprises an upper piston member and a lower piston member, and
wherein the at least one resilient member is operatively connected to and positioned between the upper piston member and the lower piston member.

5. The muscle-powered pulsation device as recited in claim 1, wherein the volume amplification module further comprises an inlet port configured to be connected directly to an outlet port of the muscle energy converter device.

6. The muscle-powered pulsation device as recited in claim 1, wherein the interior cavity of the casing defines a third chamber positioned between the first chamber and the inlet of the volume amplification module, the third chamber being in fluid communication with the outlet of the muscle energy converter device.

7. The muscle-powered pulsation device as recited in claim 6, wherein the third chamber is in fluid communication with the first chamber.

8. The muscle-powered pulsation device as recited in claim 1, wherein the piston arrangement of the muscle energy converter device is mechanically connected to the at least one piston member of the volume amplification module via a piston rod.

9. A muscle-powered pulsation system, comprising:
a muscle energy converter device configured to direct fluid out of an outlet of the muscle energy converter device using energy provided by a patient's muscle;
a hydraulic volume amplification module fluidly connected to the muscle energy converter device; and
a balloon pump fluidly connected to the volume amplification module,
wherein the volume amplification module is configured to amplify a volume of the fluid directed from the muscle energy converter device to the balloon pump.

10. The muscle-powered pulsation system as recited in claim 9, wherein the balloon pump comprises an extra-aortic balloon pump.

11. The muscle-powered pulsation system as recited in claim 9, wherein the balloon pump comprises a first plurality of tubes separated from a second plurality of tubes by at least one sidewall.

12. The muscle-powered pulsation system as recited in claim 11, wherein the balloon pump includes two separate sidewalls configured to separate the first plurality of tubes and the second plurality of tubes.

13. The muscle-powered pulsation system as recited in claim 9, wherein the balloon pump comprises a sleeve configured to compress ventricles of a patient's heart.

14. The muscle-powered pulsation system as recited in claim 9, further comprising a connecting conduit fluidly connecting the volume amplification module and the balloon pump.

15. The muscle-powered pulsation system as recited in claim 9, wherein the volume amplification module comprises:
a casing;
at least one resilient member positioned within an interior cavity defined by the casing; and
at least one piston member movably positioned within the interior cavity of the casing, the at least one piston member separating the interior cavity into a first chamber and a second chamber.

16. The muscle-powered pulsation system as recited in claim 15, wherein the at least one resilient member comprises at least one bellows.

17. The muscle-powered pulsation system as recited in claim 16,
wherein the at least one piston member comprises a pair of piston members, and
wherein a first piston member is connected to a first bellows and a second piston member is connected to a second bellows.

18. The muscle-powered pulsation system as recited in claim 15,
wherein the at least one piston comprises an upper piston member and a lower piston member, and
wherein the at least one resilient member is operatively connected to and positioned between the upper piston member and the lower piston member.

19. The muscle-powered pulsation system as recited in claim 15, wherein a piston arrangement of the muscle energy converter device is mechanically connected to the at least one piston of the volume amplification module via a piston rod.

20. A method for moving fluid in a patient using a muscle of a patient, comprising:
rotating an actuator arm mechanism against a bellows mechanism in a casing when the muscle pulls the actuator arm mechanism;
rotating a rotary cam of the actuator arm mechanism against a roller bearing cam follower;
forcing fluid out of an outlet port of the casing into a volume amplification module;
forcing the fluid against a nested bellow and piston arrangement positioned within the volume amplification module; and
forcing a supplemental fluid out of an outlet port of the volume amplification module.

21. The method recited in claim 20, further comprising directing the supplemental fluid from the outlet port of the volume amplification module to a balloon pump.

22. The method recited in claim 21, further comprising inflating the balloon pump with the supplemental fluid to compress an aorta of the patient.

23. The method recited in claim 22, wherein the balloon pump is inflated with the supplemental fluid while a heart of the patient is relaxed.

24. The method recited in claim 21, further comprising inflating the balloon pump with the supplemental fluid to compress ventricles of the patient.

25. The method recited in claim 24, wherein the balloon pump is inflated with the supplemental fluid during a diastole cycle.

26. The method recited in claim 20, wherein the volume amplification module comprises:
- a module casing comprising an inlet and an outlet, the inlet in fluid communication with an outlet of the casing;
- at least one resilient member positioned within an interior cavity defined by the module casing; and
- at least one piston member movably and sealingly positioned within the interior cavity of the module casing and operatively connected to the at least one resilient member, the at least one piston member separating the interior cavity into a first chamber and a second chamber.

* * * * *

UNITED STATES PATENT AND TRADEMARK OFFICE
CERTIFICATE OF CORRECTION

| | |
|---|---|
| PATENT NO. | : 11,391,268 B2 |
| APPLICATION NO. | : 16/617706 |
| DATED | : July 19, 2022 |
| INVENTOR(S) | : Jooli Han et al. |

It is certified that error appears in the above-identified patent and that said Letters Patent is hereby corrected as shown below:

In the Specification

Column 1, Line 12, Delete "hare" and insert -- are --

Column 1, Line 12, Delete "in" and insert -- by --

Signed and Sealed this
Twenty-fifth Day of October, 2022

Katherine Kelly Vidal
*Director of the United States Patent and Trademark Office*